US010155945B2

(12) United States Patent
Knopov et al.

(10) Patent No.: US 10,155,945 B2
(45) Date of Patent: Dec. 18, 2018

(54) METHOD OF PRODUCING LIPID NANOPARTICLES FOR DRUG DELIVERY

(71) Applicant: Nitto Denko Corporation, Osaka (JP)

(72) Inventors: Victor Knopov, Oceanside, CA (US); Richard P. Witte, San Diego, CA (US); Priya Karmali, San Diego, CA (US); Robin Lee, San Diego, CA (US); David Webb, Oceanside, CA (US); Violetta Akopian, Oceanside, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 15/430,387

(22) Filed: Feb. 10, 2017

(65) Prior Publication Data
US 2017/0152516 A1    Jun. 1, 2017

Related U.S. Application Data

(63) Continuation of application No. 13/669,078, filed on Nov. 5, 2012, now Pat. No. 9,579,338, which is a continuation of application No. PCT/US2012/063457, filed on Nov. 2, 2012.

(60) Provisional application No. 61/556,124, filed on Nov. 4, 2011.

(51) Int. Cl.
| C12N 15/113 | (2010.01) |
| A61K 31/7105 | (2006.01) |
| A61K 9/00 | (2006.01) |
| A61K 9/10 | (2006.01) |
| A61K 9/127 | (2006.01) |
| A61K 9/19 | (2006.01) |
| A61K 31/713 | (2006.01) |
| A61K 47/12 | (2006.01) |
| A61K 47/26 | (2006.01) |

(52) U.S. Cl.
CPC .......... *C12N 15/113* (2013.01); *A61K 9/0019* (2013.01); *A61K 9/10* (2013.01); *A61K 9/1271* (2013.01); *A61K 9/1272* (2013.01); *A61K 9/1277* (2013.01); *A61K 9/19* (2013.01); *A61K 31/713* (2013.01); *A61K 31/7105* (2013.01); *A61K 47/12* (2013.01); *A61K 47/26* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| 4,781,871 A | 11/1988 | West, III et al. |
| 4,895,452 A | 1/1990 | Yiournas et al. |
| 5,653,996 A | 8/1997 | Hsu |
| 6,843,942 B2 | 1/2005 | Katinger et al. |
| 6,858,225 B2 | 2/2005 | Semple et al. |
| 7,094,423 B1 | 8/2006 | Maurer et al. |
| 7,223,887 B2 | 5/2007 | Gaucheron et al. |
| 7,691,405 B2 | 4/2010 | Chen et al. |
| 7,901,708 B2 | 3/2011 | MacLachlan et al. |
| 2004/0142025 A1 | 7/2004 | MacLachlan et al. |
| 2009/0048197 A1 | 2/2009 | Chen et al. |
| 2009/0191259 A1 | 7/2009 | Li et al. |
| 2009/0312402 A1 | 12/2009 | Contag et al. |
| 2010/0041152 A1 | 2/2010 | Wheeler et al. |
| 2011/0024929 A1 | 2/2011 | Nakamura et al. |
| 2011/0038941 A1 | 2/2011 | Lee et al. |
| 2011/0117125 A1 | 5/2011 | Hope et al. |
| 2011/0177130 A1 | 7/2011 | Maurer et al. |
| 2011/0256059 A1 | 10/2011 | Sanchez Barreiro et al. |
| 2012/0225129 A1 | 9/2012 | Eliasof et al. |

FOREIGN PATENT DOCUMENTS

| CN | 102231952 A | 11/2011 |
| CN | 103857654 A | 6/2014 |
| JP | 2002-501511 | 1/2002 |
| JP | 2015-502345 A | 1/2015 |
| RU | 2573409 C2 | 1/2016 |
| WO | WO 1998/051278 A2 | 11/1998 |
| WO | WO 2001/005373 A1 | 1/2001 |
| WO | WO 2007/051303 A1 | 5/2007 |
| WO | WO 2010/021865 A1 | 2/2010 |
| WO | WO 2010/056403 A1 | 5/2010 |
| WO | WO 2010/080724 A1 | 7/2010 |
| WO | WO 2011/068810 A1 | 6/2011 |
| WO | WO 2011/090965 A1 | 7/2011 |
| WO | WO 2011/127255 A1 | 10/2011 |
| WO | WO 2011/140627 A1 | 11/2011 |
| WO | WO 2012/170952 A1 | 12/2012 |
| WO | WO 2013/064911 A2 | 5/2013 |

OTHER PUBLICATIONS

U.S. Appl. No. 13/669,217, filed Nov. 5, 2012, Knopov.
Batzri et al., "Single bilayer liposomes prepared without sonication," Biochim. Biophys. Acta, Apr. 1973, 298(4), 1015-1019.
Hirota et al., "Simple mixing device to reproducibly prepare cationic lipid-DNA complexes (lipoplexes)," BioTechniques, Aug. 1999, 27(2), 286-290.
International Patent Application No. PCT/US2012/063457: International Search Report and Written Opinion dated Feb. 21, 2013, 15 pages.
Maurer et al., "Spontaneous Entrapment of Polynucleotides upon Electrostatic Interaction with Ethanol-Destabilized Cationic Liposomes," Biophysical J., May 2001, 80(5), 2310-2326.
Yadava et al., "Effect of Lyophilization and Freeze-thawing on the Stability of siRNA-liposome Complexes," AAPS PharmSciTech, Jun. 2008, 9(2), 335-341.

(Continued)

*Primary Examiner* — Celeste A Roney
(74) *Attorney, Agent, or Firm* — Baker & Hostetler LLP

(57) ABSTRACT

What is described is a method for preparing a liposome that efficiently encapsulates a negatively charged therapeutic polymer, e.g., siRNA. The process involves preparing a lipid mixture comprising a cationic lipid in a water miscible organic solvent, such as ethanol, at a concentration of 2.3 mg/ml, and adding this solution to the polymer dissolved in water to a final concentration of 35% ethanol in water. The final charge ratio of drug:lipid is 1:2.5. The resulting nanoparticles have a mean size of 50 to 150 nm.

23 Claims, 6 Drawing Sheets

(56) References Cited

OTHER PUBLICATIONS

China Patent Application No. 201280054027.8; Office Action; dated Aug. 7, 2015; 18 pages.

Taiwan Patent Application No. 101141082; Office Action; dated Jul. 6, 2016; 12 pages (translation).

China Patent Application No. 201280054027.8; Office Action; dated Jun. 28, 2016; 19 pages (translation).

Japan Patent Application No. 2014-540573; Office Action—Reasons for Refusal; dated Jul. 25, 2016; 13 pages.

Kowtoniuk et al.; "A Chemical Screen for Biological Small Molecule—RNA Conjugates Reveals CoA-Linked RNA"; Proc Nat'l Acad. Sci. USA; vol. 106 No. 19; May 2009; pp. 7768-7773.

Rabinovich et al.; Quick Chemical Reference Book; Himiya 1991; see p. 283 (English Translation).

Russia Patent Application No. 2014122432/15; Office Action dated; Dec. 7, 2016; 14 pages. (English Translation).

Kremer et al.; "Vesicles of Variable Diameter Prepared by a Modified Injection Method"; Biochemistry; vol. 16 No. 17; 1977; p. 3932-3935.

Allison et al.; "Stabilization of lipid/DNA complexes during the freezing step of the lyophilization process: the particle isolation hypothesis"; Biochimica (BBA); vol. 1468 Issues 1-2; Sep. 2000; p. 127-138.

Armstrong et al.; "Immobilization of Nonviral Vectors During the Freezing Step of Lyophilization"; Journal of Pharmaceutical Sciences; vol. 93 Issue 11; Nov. 2004; p. 2698-2709.

European Patent Application No. 12848760.0; Office Action—Article 94(3); dated May 31, 2016; 7 pages.

European Patent Application No. 12848760.0; Office Action—Article 94(3); dated Aug. 24, 2017; 6 pages.

European Patent Application No. 12848760.0; Office Action—Article 94(3); dated Jun. 29, 2018; 6 pages.

Taiwan Patent Application No. 10114102; Office Action; dated Feb. 20, 2017; 10 pages.

Japan Patent Application No. 2017-083327; Reasons for Refusal; dated Feb. 27, 2018; 4 pages.

METHOD OF PRODUCING LIPID NANOPARTICLES FOR DRUG DELIVERY

CROSS REFERENCE TO RELATED APPLICATION

This application is a continuation of U.S. application Ser. No. 13/669,078, filed Nov. 5, 2012, now U.S. Pat. No. 9,579,338, issued Feb. 28, 2017, which is a continuation of PCT Application No. PCT/US12/63457 filed Nov. 2, 2012, which claims the benefit of U.S. Provisional Application No. 61/556,124 filed Nov. 4, 2011, each of which is hereby incorporated by reference in its entirety.

TECHNICAL FIELD

The description is directed to a method of forming lipid-nucleic acid particles simply and reproducibly. The method produces particles that are monodisperse with a mean size 50-150 nm.

BACKGROUND

Lipids are potentially useful as carriers for delivery of therapeutic molecules, particularly for delivery of nucleic acids. Lipids form liposomes, which can encapsulate, complex, or entrap nucleic acid molecules and thereby enhance delivery of this class of therapeutic molecules to target cells upon administration, e.g., intravenously to the circulation. Their usefulness in pharmaceutical compositions is limited by available methods to produce lipid-nucleic acid nanoparticles reproducibly. Various methods have been devised to produce such nanoparticles.

Batzri et al., 1973, Biophys Biochem Acta 298:1015-19, and Kremer et al., 1977, Biochemistry 16:3932-35, describe producing lipid vesicles by dissolving lipids in ethanol and injecting the ethanol solution into an aqueous solution in which the lipids spontaneously form liposomes. Hirota et al., 1999, BioTechniques 27:286-89, describe producing lipid vesicles coated with nucleic acid molecules by dissolving cationic lipids in ethanol and injecting the ethanol solution into an aqueous solution containing the nucleic acid molecules. This method fails to produce liposomes that encapsulate nucleic acid.

Maurer et al. U.S. Pat. No. 7,094,423 describe producing liposomes that encapsulate nucleic acids by first preparing preformed single-walled lipid vesicles in an aqueous solution. The preformed lipid vesicles are prepared by dissolving lipids in ethanol, and injecting the lipid mixture into an aqueous buffer. The process of preparing empty preformed vesicles includes sizing by extrusion. Ethanol is added to the empty preformed vesicles after sizing to destabilize them, and nucleic acids in 40% ethanol is added to the destabilized lipid vesicles. After incubation, the mixture is diafiltered to remove ethanol. Variations in the percentage ethanol, temperature, incubation time, lipid composition, drug/lipid ratio, and initial nucleic acid concentration all influence the encapsulation efficiency and yield of this method. For example, Maurer et al. discloses that entrapment increases with increasing oligonucleotide:lipid ratio, reaching a maximum at more than 0.16 mg antisense oligonucleotide per mg lipid, while producing an increase in the number of larger liposomes and in their polydispersity.

Semple et al. U.S. Pat. No. 6,858,225 produce liposomes encapsulating RNA using an ionizable cationic lipid. The lipid is dissolve in ethanol and is combined with nucleic acids in an aqueous buffer at low pH. The ethanol is removed and the pH is brought to neutral pH to form the liposomes. The resulting liposomes are heterogeneous and require homogenization or extrusion to obtain monodisperse lipid vesicles. Consistent with Maurer et al., Semple et al. disclose that entrapment increases with increasing oligonucleotide:lipid ratio, reaching a maximum at more than 0.16 mg antisense oligonucleotide per mg lipid, while producing an increase in the number of larger liposomes and in their polydispersity.

MacLachlan et al. U.S. Pat. No. 7,901,708 describe producing lipid vesicles encapsulating RNA by mixing lipids dissolved in ethanol with RNA in an aqueous solution in a mixing chamber (T-tube) in which the lipids and RNA are diluted stepwise, thereby substantially instantaneously forming vesicles.

Wheeler et al. US 20100041152 describe producing liposomes encapsulating RNA by dissolving cationic lipids in ethanol and mixing with RNA in 65-85% ethanol to produce a soluble, charge-neutralized complex, adding non-cationic lipids to this complex to form a lipid-nucleic acid mixture, and removing ethanol. The liposomes require homogenization or extrusion to obtain monodisperse lipid vesicles.

There remains an unmet need for a manufacturing method to encapsulate nucleic acids without the need for extensive mechanical processing steps to prepare preformed liposomes and without the need for processing step to reduce lipid-nucleic acid particles to a monodisperse population.

SUMMARY

One aspect of the description is a method for preparing a lipid nanoparticle encapsulating a polyanion, comprising the steps of adding a first solution comprising lipids dissolved in an water-miscible organic solvent at a constant rate into a second solution comprising the polyanion in an aqueous buffer while stirring the second solution to produce a mixture comprising the organic solvent at 25-45% (v:v); and removing the organic solvent from the mixture by diafiltration against an aqueous buffered solution at neutral pH. Addition of the first solution to the second solution is preferably completed in 1-100 minutes. The polyanion may be a nucleic acid, e.g., an RNA molecule. The polyanion preferably is at a concentration of 0.08 to 0.8 mg/ml. The drug:lipid ratio (w:w) of the lipid nanoparticle preferably is 0.06 to 0.16. The drug:lipid charge ratio of the lipid nanoparticle preferably is 1:2.5 to 1:1.

Another embodiment of method is use of a polysaccharide in the aqueous solutions. The polysaccharide preferably is selected the group consisting from sucrose, trehalose, mannitol, sorbitol, xylitol, lactose, maltose and inulin. Another embodiment of the method further comprises the step of lyophilizing the lipid nanoparticle encapsulating the polyanion.

In another embodiment of the method, the organic solution preferably is ethanol. Preferably, upon completing mixture of the lipid and the polyanion, the mixture comprises ethanol at 35% (v:v).

In another embodiment of the method, the lipids comprise a cationic lipid, a helper lipid, a sterol, and a PEG lipid. Preferably, the cationic lipid is 40 to 60 mole percent of the lipids. Preferably, the cationic lipid is selected from the group consisting of HEDC, HEDODC and HE-Et-DODC, described herein, more preferably one consisting of an ionizable or non-ionizable positive charge. Preferably, the lipids further comprise a targeting lipid.

In another embodiment of the method, the ethanol and aqueous solutions are mixed at 25-55° C., and buffered at pH 3.5-6.5, preferably with citrate.

Another aspect of the description is a pharmaceutical formulation comprising a lipid nanoparticle encapsulating a polyanion produced by a process comprising the steps of adding a first solution comprising lipids dissolved in an water-miscible organic solvent at a constant rate into a second solution comprising the polyanion in an aqueous buffer while stirring the second solution to produce a mixture comprising the organic solvent at 25-45% (v:v); and removing the organic solvent from the mixture by diafiltration against an aqueous buffered solution at neutral pH.

An embodiment includes a pharmaceutical formulation comprising a nucleic acid, a RNA molecule, or a double stranded siRNA molecule. Preferably, the drug:lipid ratio of the lipid nanoparticle is 0.06 to 0.16 (w:w), and the drug:lipid charge ratio of the lipid nanoparticle is 1:25:1 to 1:1.

In another embodiment of the pharmaceutical formulation, the lipids comprise a cationic lipid, a helper lipid, a sterol, and a PEG lipid. Preferably, the cationic lipid is 40 to 60 mole percent of the lipids. The cationic lipid preferably is selected from the group consisting of HEDC, HEDODC and HE-Et-DODC. The cationic lipid may consist of an ionizable or non-ionizable positive charge. The lipids may further comprise a targeting lipid.

Another embodiment of the pharmaceutical formulation further comprises a polysaccharide, preferably selected the group consisting from sucrose, trehalose, mannitol, sorbitol, xylitol, lactose, maltose and inulin. Preferably the process to produce the pharmaceutical formulation further comprises lyophilization of the liposome-encapsulated polyanion. The pharmaceutical formulation may further comprised citrate. The pharmaceutical formulation may further comprise processing aids consisting of poloxamers, surfactants, detergents, or polyhydroxy or polyhydroxyethylene polymers.

In another embodiment, the pharmaceutical formulation consists of lipid nanoparticles encapsulating RNA molecules having a mean particle diameter of 50-150 nm, more preferably less than 100 nm, most preferably minimally polydisperse.

DETAILED DESCRIPTION OF ILLUSTRATIVE EMBODIMENTS

Figure 1:
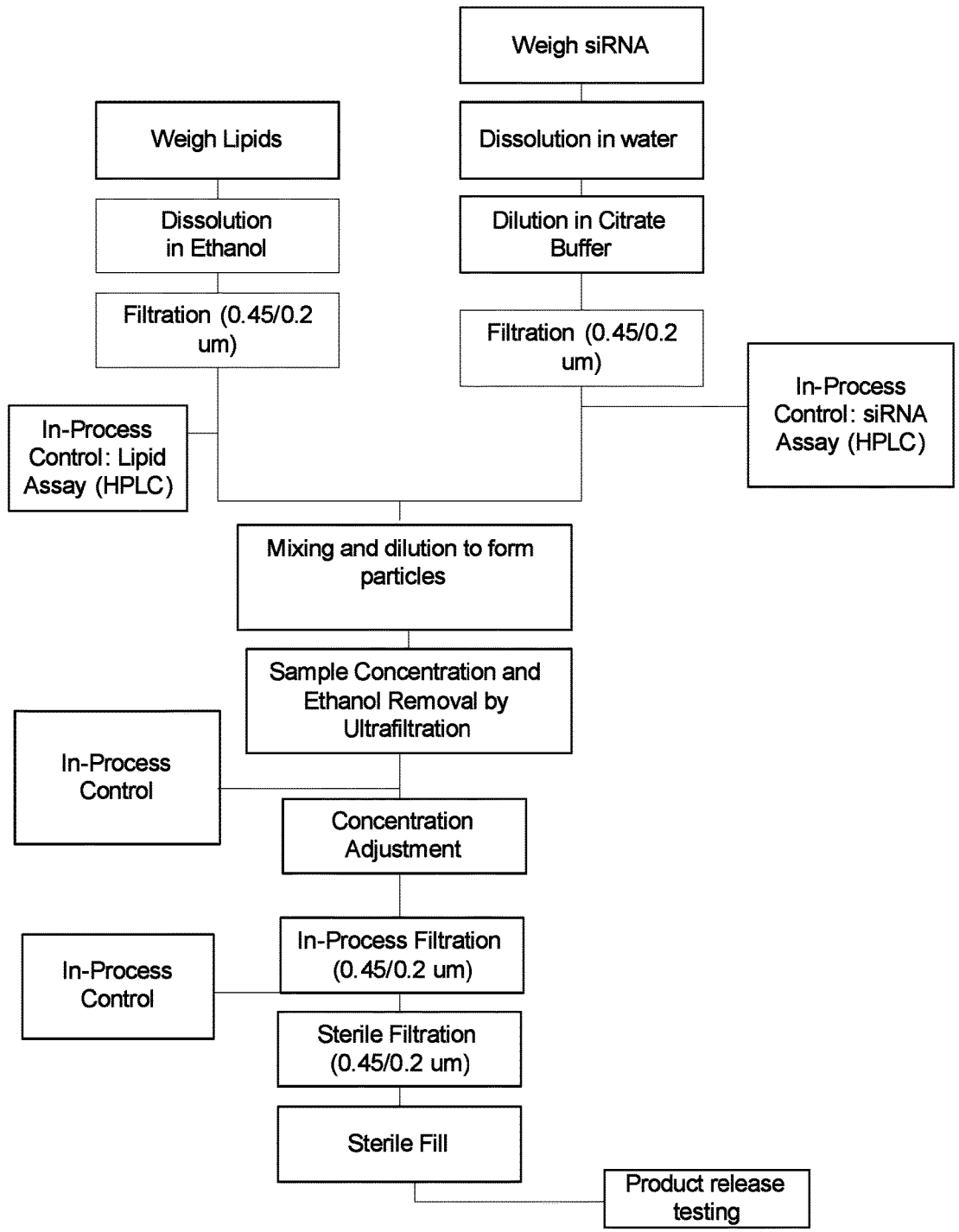
FIG. 1 shows a schematic of the process described herein for preparing lipid-nucleic acid nanoparticles. The details of each step of the process are described below.

The description herein provided relates to a method for making lipid-encapsulated therapeutic molecules, including negatively-charged therapeutic polymers, e.g., nucleic acids, proteins, and peptides. The description herein provided includes a method for making lipid-encapsulated nucleic acid molecules. The method is particularly amenable to large-scale manufacture of particles consisting of liposome-encapsulated therapeutic molecules. The method provides the unexpected and surprising result that the particles produced are a size distribution between 50 and 150 nm with a polydispersity index (PDI) less than 0.2. This method provides a means of encapsulating by combining lipids solubilized in a water-miscible organic solvent, such as ethanol, with negatively-charged therapeutic polymers solubilized in an aqueous solution, and removing the organic solvent. The absolute and relative concentrations of the lipids and negatively-charged therapeutic polymers are sufficient to produce small particles. The particles produced by the method of the description do not require mechanical processing, such as extrusion, to obtain a particle population with a PDI less than 0.2.

The method of the description has the advantage over previous methods by the ease in which it can be scaled up to large volumes and that it is robust over a wide range of temperatures, solutes, pH, and processing times.

The method of the description has the advantage over previous methods by reproducibly producing a population of particles with a PDI less than 0.2, preferably, less than 0.1, and without extra steps required to produce preformed vesicles.

The method of the description has the advantage over previous methods by reproducibly producing a uniform population of nanoparticles without extra steps required to mechanically process particles produced upon mixture of lipids and negatively charged therapeutic polymers. These extra steps include, for example sonication, homogenization, or extrusion, to reduce their size and achieve uniformity to a therapeutically acceptable range.

The method of the description has the advantage of achieving nucleic acid encapsulation efficiency equal to or better than previous methods without extra processing steps to produce nanoparticles.

Other advantages of the method of the description will become apparent as further detail is provided in the description herein regarding lipid components and conditions.

The lipid mixture used in the method of the description contains at least a positively charged lipid (cationic lipid) to complex with the negatively-charged therapeutic polymers, and a polyethylene glycol-containing lipid conjugate (PEG-lipid) to prevent aggregation. The cationic lipid can be a permanent cationic charge over a wide range of pH conditions, an ionizable cationic lipid, which is charged at low pH (less than pH 6) and without a net charge at neutral pH (pH 6.5 to 8), or a combination of permanent and ionizable cationic lipids. The lipid mixture can also contain a targeting lipid, a polymer, a steroid, a phospholipid, or a member of another lipid group, including a fat, a wax, fat-soluble vitamin, monoglyceride or diglyceride, fatty acyls, glycerolipids, glycerophospholipids, sphingolipids, saccharolipids and polyketides. This method can also be used for the formation of liposomes with only neutral or negatively charged components.

Preferentially the components of the lipid mixture may be selected from the following groups.

Cationic Lipid

Within the scope of the description are cationic lipids of formula I

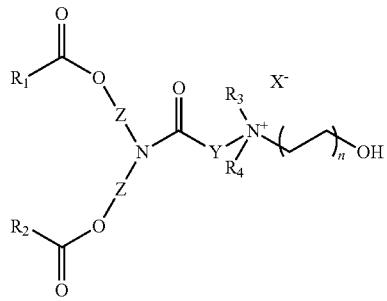

in which

Z=an alkyl linker, $C_2$-$C_4$ alkyl

Y=an alkyl linker, $C_1$-$C_6$ alkyl $R_1$ and $R_2$ are each independently $C_{10}$-$C_{30}$alkyl, $C_{10}$-$C_{30}$alkenyl, or $C_{10}$-$C_{30}$alkynyl, $C_{10}$-$C_{30}$alkyl, $C_{10}$-$C_{20}$alkyl, $C_{12}$-$C_{18}$alkyl, $C_{13}$-$C_{17}$alkyl, $C_{13}$alkyl, $C_{10}$-$C_{30}$alkenyl, $C_{10}$-$C_{20}$alkenyl. $C_{12}$-$C_{18}$alkenyl, $C_{13}$-$C_{17}$alkenyl, $C_{17}$alkenyl; $R_3$ and $R_4$ are each independently hydrogen, $C_1$-$C_6$alkyl, or —$CH_2CH_2OH$, $C_1$-$C_6$alkyl, $C_1$-$C_3$alkyl; n is 1-6; and X is a counterion, including any nitrogen counterion, as that term is readily understood in the art. Preferred nitrogen counterion include halogens, with chloride and bromide being particularly preferred. Another preferred counterion is mesylate (—$SO_3CH_3$).

Exemplary compounds of formula I include:

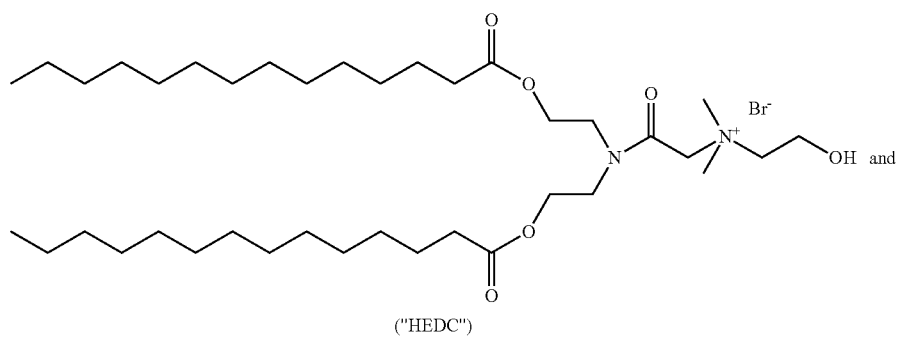

("HEDC")

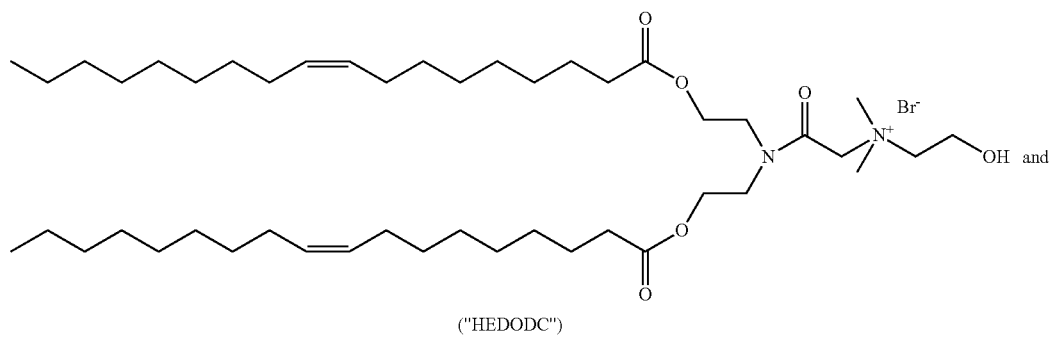

("HEDODC")

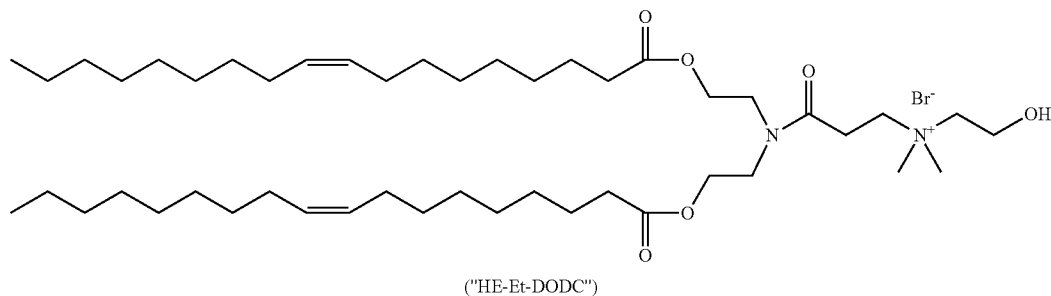

("HE-Et-DODC")

Other cationic charged lipids at physiological pH include, but are not limited to, N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleyloxy)propyl)-N,N,N-trimethylammonium chloride ("DOTAP"); N-(1,2-dimyristyloxyprop-3-yl)-N,N-dimethyl-N-hydroxyethylammonium bromide ("DMRIE"), 3β-(N—(N',N'-dimethylaminoethane)carbamoyl)cholesterol ("DC-Chol"), dioctadecylamidoglycyl carboxyspermidine ("DOGS"); and N-(1-(2,3-dioleyloxy)propyl)-N-(2-(sperminecarboxamido)ethyl)-N,N-dimethylammonium trifluoroacetate ("DOSPA").

Ionizable Cationic Lipids.

Within the scope of the description are ionizable cationic lipids of formula II

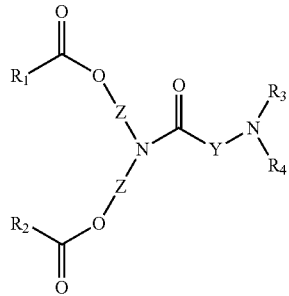

II in which

Z=an alkyl linker, $C_2$-$C_4$ alkyl, —$CH_2SCH_2CH_2$—

Y=an alkyl linker, $C_1$-$C_6$ alkyl $R_1$ and $R_2$ are each independently $C_{10}$-$C_{30}$alkyl, $C_{10}$-$C_{30}$alkenyl, or $C_{10}$-$C_{30}$alkynyl, $C_{10}$-$C_{30}$alkyl, $C_{10}$-$C_{20}$alkyl, $C_{12}$-$C_{18}$alkyl, $C_{13}$-$C_{17}$alkyl, $C_{13}$alkyl, $C_{10}$-$C_{30}$alkenyl, $C_{10}$-$C_{20}$alkenyl. $C_{12}$-$C_{18}$alkenyl, $C_{13}$-$C_{17}$alkenyl, $C_{17}$alkenyl; $R_3$ and $R_4$ are each independently hydrogen, $C_1$-$C_6$alkyl, or —$CH_2CH_2OH$, $C_1$-$C_6$alkyl, $C_1$-$C_3$alkyl.

Some positively charged lipids have a pKa at or near physiological pH and are cationic in mild acid conditions and weakly cationic at physiological pH. Such ionizable cationic lipids include, but are not limited to, ((2-((2-(dimethylamino)ethyl)thio)acetyl)azanediyl)bis(ethane-2,1-diyl) ditetradecanoate ("S104"), (Z)-((3-(dimethylamino)propanoyl)azanediyl)bis(ethane-2,1-diyl) dioleate ("i-Et-DODC"), dioleyloxy)propyl)N,N-dimethylammonium chloride ("DODMA") and 1,2-dioleoyl-3-dimethylammonium-propane ("DODAP").

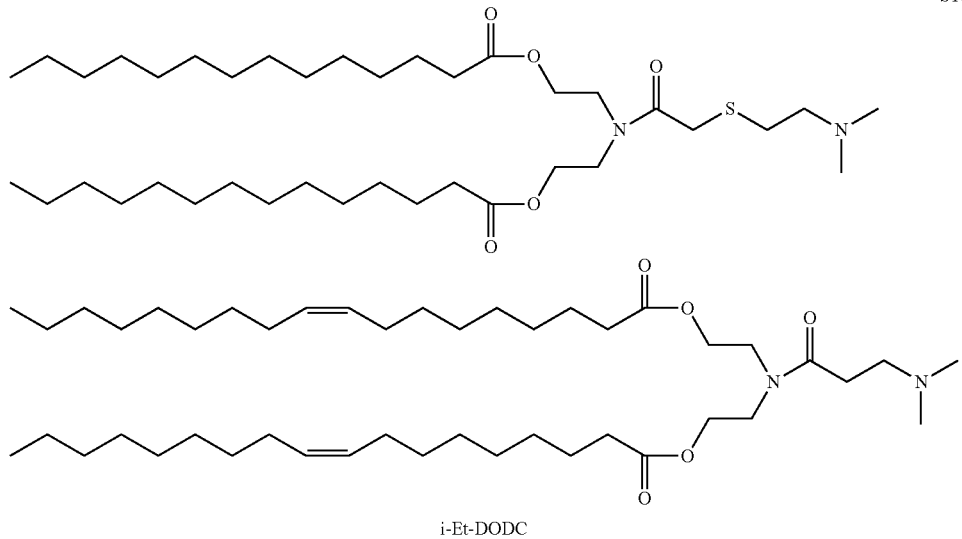

i-Et-DODC

It is recognized that ionizable lipids may facilitate the binding and/or release of the active pharmaceutical ingredient (API), as shown below.

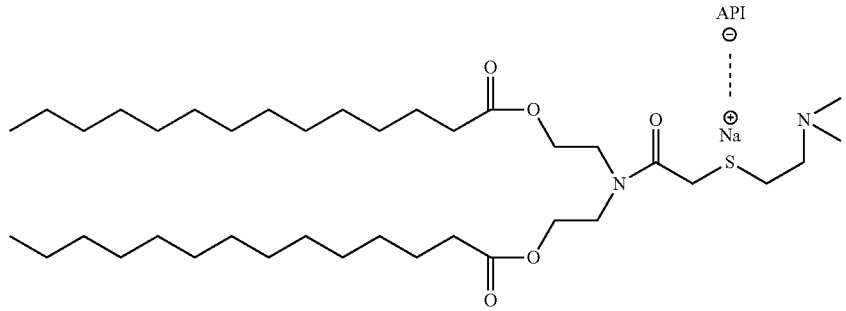

Neutral Lipids

Examples of neutral lipids include, but are not limited to, phospholipids, aminolipids and sphingolipids. Neutral lipids include amphipathic lipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid, glycosphingolipid families, diacylglycerols and 3-acyloxyacids, are also within the group designated as amphipathic lipids. Additionally, the amphipathic lipid described above can be mixed with other lipids including triglycerides and sterols.

PEG-Lipids

A bilayer stabilizing component is polyethylene glycol ("PEG") conjugated to a lipid head group, e.g., phosphatidylethanolamine. Another bilayer stabilizing component is PEG conjugated to a ceramide. PEG can be conjugated to a phosphatidylethanolamine or, alternatively, to a ceramide using standard coupling reactions known to and used by those of skill in the art. In addition, preformed PEG-phosphatidylethanolamine ("PEG-PE") conjugates are commercially available.

PEGs of varying molecular weights can be used to form the bilayer stabilizing components of the present invention. PEGs of varying molecular weights are commercially available from a number of different sources or, alternatively, they can be synthesized using standard polymerization techniques well-known to those of skill in the art. In a presently preferred embodiment, the polyethylene glycol has a molecular weight ranging from 200 to 10000 Da, preferably 500 to 4000 Da, and most preferably 1000 to 2000 Da. Generally, it has been found that increasing the molecular weight of the PEG reduces the concentration of the bilayer stabilizing component required to achieve stabilization.

Phosphatidylethanolamine having a variety of acyl chain groups of varying chain lengths and degrees of saturation can be conjugated to PEG to form the bilayer stabilizing component. Such phosphatidylethanolamines are commercially available, or can be isolated or synthesized using conventional techniques known to those of skill in the art. Phosphatidylethanolamines containing saturated or unsaturated fatty acids with carbon chain lengths in the range of C10 to C20 are preferred. Phosphatidylethanolamines with mono- or diunsaturated fatty acids and mixtures of saturated and unsaturated fatty acids can also be used. Suitable phosphatidylethanolamines include, but are not limited to, the following: dimyristoylphosphatidylethanolamine (DMPE), dipalmitoylphosphatidylethanolamine (DPPE), dioleoylphosphatidylethanolamine (DOPE) and distearoylphosphatidyl-ethanolamine (DSPE).

The forgoing compositions can also include PEG-conjugated lipids, which are known in the art per se, including PEG-phospholipids and PEG-ceramides, including one or more molecules selected from the following: PEG2000-DSPE, PEG2000-DPPE, PEG2000-DMPE, PEG2000-DOPE, PEG1000-DSPE, PEG1000-DPPE, PEG1000-DMPE, PEG1000-DOPE, PEG550-DSPE, PEG550-DPPE, PEG-550DMPE, PEG-1000DOPE, PEG-cholesterol, PEG2000-ceramide, PEG1000-ceramide, PEG750-ceramide, and PEG550-ceramide.

Furthermore, compositions can also include monodisperse (md) PEG-lipids, with general formula mdPEG-linker-lipid, with examples including, but not limited to, 83-hydroxy-3,6,9,12,15,18,21,24,27,30,33,36,39,42,45,48,51,54,57,60,63,66,69,72,75,78,81-heptacosaoxatrioctacontyl (2,3-bis(tetradecyloxy)propyl)carbamate ("HO-PEG1251-cBTP") and 134-hydroxy-3,6,9,12,15,18,21,24,27,30,33,36,39,42,45,48,51,54,57,60,63,66,69,72,75,78,81,84,87,90,93,96,99,102,105,108,111,114,117,120,123,126,129,132-tetratetracontaoxatetratriacontahectyl (2,3-bis(tetradecyloxy)propyl)carbamate ("HO-PEG2000-cBTP") as examples.

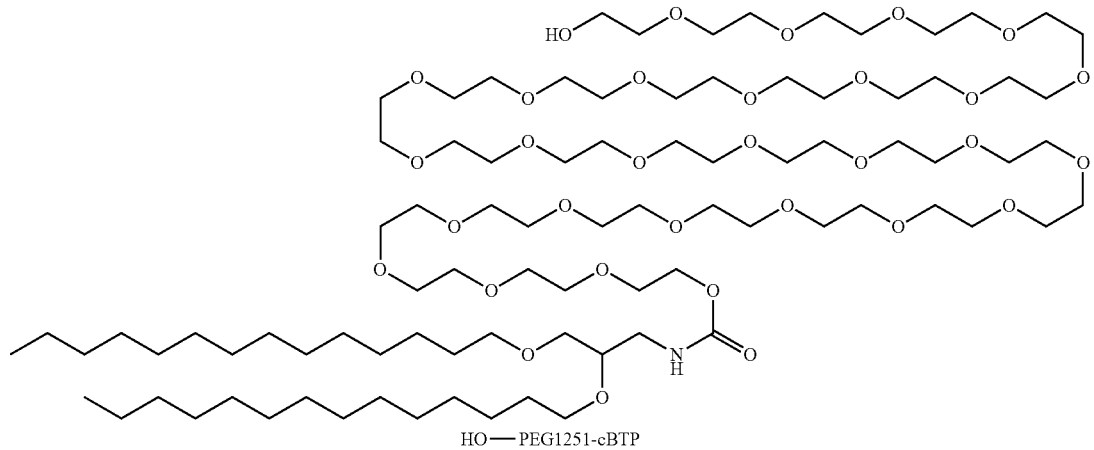

HO—PEG1251-cBTP

-continued

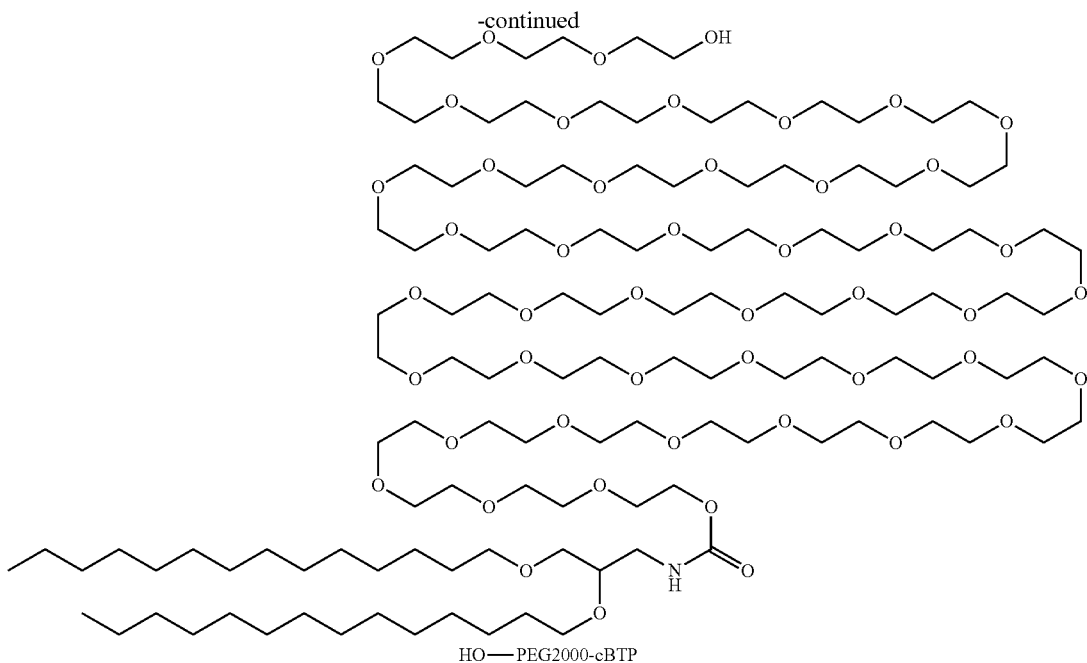

HO—PEG2000-cBTP

Steroids

Steroids include cholestanes (e.g., cholesterol), cholanes and bile acids (e.g., chenodeoxycholate and cholate), ergosterol, lanosterol, corticosteroids (e.g., glucocorticoid), pregnane (e.g., progesterone), and phytosterols. These can be included also in the form of a conjugate with a hydrophilic moiety, e.g., a polyethylene glycol. A preferred steroid is cholesterol.

Targeting Lipid

An example of a targeting lipid is a compound of the formula (A),

L-X—R　　　　　　　　　　　　　　　A in which
  lipid (L) is selected from the group consisting of DSPE, DOPE, and DC;
  linker (X) is selected from the group consisting of nothing, PEG550, PEG2000, PEG-glutamate (-Glu), Glu, C6, glycine, and GluNH, N1,N19-bis(3-(2-(2-(3-aminopropoxy)ethoxy)ethoxy)propyl)-4,7,10,13,16-pentaoxanonadecane-1,19-diamide; and
  retinoid (R) is selected from the group consisting of tretinoin, adapalene, retinol, 4-hydroxy(phenyl)retinamide (4-HPR), retinoic acid (vitamin A), 9-(2,6,6-trimethylcyclohex-1-en-1-yl)nonanoic acid, 3,7-dimethyl-9-(2,6,6-trimethylcyclohex-1-en-1-yl)nonanoic acid, 3,7-dimethyl-9-(2,2,6-trimethylcyclohexyl) nonanoic acid, and any partially or fully saturated retinoid or a derivative thereof.

Another example of a targeting lipid is a compound of the formula (B),

R—X—R　　　　　　　　　　　　　　　B, in which
  linker (X) is N1,N19-bis(3-(2-(2-(3-aminopropoxy) ethoxy)ethoxy)propyl)-4,7,10,13,16-pentaoxanonadecane-1,19-diamide ("bisamido-PEG") or N1,N19-bis (16,20-diamino-15-oxo-4,7,10-trioxa-14-azaicosyl)-4, 7,10,13,16-pentaoxanonadecane-1,19-diamide ("lys-bisamido-PEG-lys"); and
  retinoid (R) is selected from the group consisting of tretinoin, adapalene, retinol, 4-hydroxy(phenyl)retinamide (4-HPR), and retinoic acid (vitamin A), 9-(2,6,6-trimethylcyclohex-1-en-1-yl)nonanoic acid, 3,7-dimethyl-9-(2,6,6-trimethylcyclohex-1-en-1-yl)nonanoic acid, 3,7-dimethyl-9-(2,2,6-trimethylcyclohexyl) nonanoic acid, and any partially or fully saturated retinoid or a derivative thereof.

Other targeting molecules can be included in the lipid mixture, e.g., folic acid, vitamin E, peptide ligands and/or monoclonal antibodies.

Drug-Lipid Particle Compositions and Formulations

The description includes compositions comprising a lipid particle with and without an active agent, in which the active agent when present is associated with the lipid particle. In particular embodiments, the active agent is a therapeutic agent. In particular embodiments, the active agent is a negatively charged therapeutic polymer encapsulated within an aqueous interior of the lipid particle. In other embodiments, the active agent is present within one or more lipid layers of the lipid particle. In other embodiments, the active agent is bound to the exterior or interior lipid surface of a lipid particle.

In certain embodiments, lipid particles of the present invention are associated with a nucleic acid, resulting in a nucleic acid-lipid particle. In particular embodiments, the nucleic acid is fully encapsulated in the lipid particle. As used herein, the term "nucleic acid" is meant to include any oligonucleotide or polynucleotide. In particular embodiments, oligonucleotides of the present invention are 15-50 nucleotides in length.

The terms "polynucleotide" (PNA) and "oligonucleotide" herein refer to a polymer or oligomer of nucleotide or nucleoside monomers consisting of naturally occurring bases, sugars and inter-sugar (backbone) linkages. The terms "polynucleotide" and "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

Oligonucleotides may be as oligodeoxyribonucleotides or oligoribonucleotides. An oligodeoxyribonucleotide consists of a deoxyribose joined covalently to phosphate at the 5' and 3' carbons of this sugar to form a negatively charged alternating, unbranched polymer. An oligoribonucleotide consists of a similar repeating structure where each nucleotide has a ribose sugar group. Modified ribose molecules may be included in an oligoribonucleotide.

The nucleic acid that is present in a lipid-nucleic acid particle according to this invention includes any form of nucleic acid that is known. The nucleic acids used herein can be single-stranded DNA or RNA, or double-stranded DNA or RNA, or DNA-RNA hybrids or RNA-PNA and/or DNA-PNA hybrids or PNA duplexes. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include, e.g., antisense oligonucleotides, ribozymes, microRNA, and triplex-forming oligonucleotides.

Nucleic acids may be of various lengths, generally dependent upon the particular form of nucleic acid. For example, in particular embodiments, plasmids or genes may be from about 1,000 to 100,000 nucleotide residues in length. In particular embodiments, oligonucleotides may range from about 10 to 100 nucleotides in length. In various related embodiments, oligonucleotides, whether single-stranded, double-stranded, and triple-stranded, may range in length from about 10 to about 50 nucleotides, from about 21 to about 50 nucleotides, from about 15 to about 30 nucleotides, from about 20 to about 30 nucleotides in length. Polynucleotides of 50 nucleotides or less are generally termed "fragments".

In particular embodiments, an oligonucleotide (or a strand thereof) may specifically hybridize to or is complementary to a target polynucleotide. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a reduction or loss of utility or expression therefrom, and there is a sufficient degree of specific base-pairing to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, in other embodiments, this oligonucleotide includes 1, 2, or 3 base substitutions as compared to the region of a gene or mRNA sequence that it is targeting or to which it specifically hybridizes.

In particular embodiments, nucleic acid-lipid particles may be associated with RNA interference (RNAi) molecules. RNA interference methods using RNAi molecules may be used to disrupt the expression of a gene or polynucleotide of interest. siRNAs are RNA duplexes normally 15-30 nucleotides long that can associate with a cytoplasmic multi-protein complex known as RNAi-induced silencing complex (RISC). RISC loaded with siRNA mediates the degradation of homologous mRNA transcripts; therefore siRNA can be designed to knock down protein expression with high specificity. Unlike other antisense technologies, siRNA function through a natural mechanism evolved to control gene expression through non-coding RNA. This is generally considered to be the reason why their activity is more potent in vitro and in vivo than either antisense oligonucleotide or ribozymes. RNAi reagents may include DNA sense:RNA antisense hybrids, RNA sense:DNA antisense hybrids, and DNA:DNA hybrids are capable of mediating RNAi. Thus, RNAi molecules comprising any of these different types of double-stranded molecules may be used. In addition, it is understood that RNAi molecules may be used and introduced to cells in a variety of forms. Accordingly, as used herein, RNAi molecules encompasses any and all molecules capable of inducing an RNAi response in cells, including, but not limited to, double-stranded polynucleotides comprising two separate strands, i.e. a sense strand and an antisense strand, e.g., small interfering RNA (siRNA); polynucleotides comprising a hairpin loop of complementary sequences, which forms a double-stranded region, e.g., shRNAi molecules, and expression vectors that express one or more polynucleotides capable of forming a double-stranded polynucleotide alone or in combination with another polynucleotide.

RNA interference (RNAi) may be used to specifically inhibit expression of target polynucleotides. Double-stranded RNA-mediated suppression of gene and nucleic acid expression may be accomplished according to the invention by introducing dsRNA, siRNA or shRNA into cells or organisms. siRNA may be double-stranded RNA, or a hybrid molecule comprising both RNA and DNA, e.g., one RNA strand and one DNA strand, or sisiRNA.

RNAi molecules targeting specific polynucleotides can be readily prepared according to procedures known in the art. Accordingly, one skilled in the art would understand that a wide variety of different siRNA molecules may be used to target a specific gene or transcript. In certain embodiments, siRNA molecules according to the invention are double-stranded and 16-30 or 18-25 nucleotides in length, including each integer in between.

Generally, siRNA molecules are completely complementary to one strand of a target DNA molecule. In other embodiments, siRNAs may have a modified composition, such as, for example, 2'-deoxy or 2'-O-methyl modifications. However, in preferred embodiments, the entire strand of the siRNA is not made with either 2' deoxy or 2'-O-modified bases.

In certain embodiments, the present invention relates to methods and compositions for producing lipid-encapsulated nucleic acid particles in which nucleic acids are encapsulated within a lipid layer. Such nucleic acid-lipid particles, incorporating siRNA oligonucleotides, are characterized using a variety of biophysical parameters including: (1) nucleic acid to lipid ratio; (2) encapsulation efficiency; and (3) particle size. High encapsulation efficiency, good nuclease resistance and serum stability and controllable particle size, generally less than 200 nm in diameter are desirable. In addition, the nature of the nucleic acid polymer is of significance, since the modification of nucleic acids in an effort to impart nuclease resistance adds to the cost of therapeutics while in many cases providing only limited resistance. Unless stated otherwise, these criteria are calculated in this specification as follows:

Drug:lipid ratio is the amount of drug in a defined volume of preparation divided by the amount of lipid in the same volume. This may be expressed as a mole per mole basis or on a weight per weight basis, or on a weight per mole basis. For final, administration-ready formulations, the drug:lipid ratio is calculated after dialysis, chromatography and/or enzyme (e.g., nuclease) digestion has been employed to remove as much of the external drug as possible.

Encapsulation

To determine siRNA encapsulation efficiency (EE), expressed as percent encapsulated siRNA in lipid-nucleic acid particles, a RIBOGREEN® assay is utilized as follows. The procedure may be used to determine duplex and single-stranded RNA or DNA concentration in solution.

Equipment includes BioTek Instruments, Inc. FLx800™, variable pipettes, and a vortex mixer. Reagents include RNAse-free water (MILLIQ® grade, or equivalent), 20×TE buffer "RNase free" (INVITROGEN™, T11493, or equivalent), QUANT-IT™ RIBOGREEN® Reagent (INVITROGEN™, R11491), and 10% TRITON™ X-100 in water (THERMO SCIENTIFIC™, 28314, or equivalent).

Preparation of 1×TE buffer involves transfer of 38 mL of RNAse-free water into a 50 mL centrifuge tube using a 50 mL graduated cylinder; and pipetting 2 mL of 20×TE buffer solution into the centrifuge tube and mix using a vortexer.

Preparation of 2% TRITON™ X-100 and 1% TRITON™ X-100 in 1×TE Buffer, involves pipetting 2 mL or 1 mL, respectively, of 10% TRITON™ X-100 into an RNase-free 15 mL conical tube, adding 8 mL or 9 mL, respectively, of 1×TE buffer, and swirling to mix well.

Preparation of a RIBOGREEN® working solution, involves removing a frozen stock of RIBOGREEN® Reagent warming to room temperature, and diluting 1:200 with TE buffer. The centrifuge tube is wrapped in aluminum foil to prevent any excess light from reaching the solution.

A standard is prepared by preparing a RNA solution in TE buffer, and plating into a 96 well plate. Samples are diluted to a final concentration of approximately 80 µg/mL siRNA and transferred to the 96 well plate as shown in FIG. 1. The RIBOGREEN® working solution is added and mixed with each sample and standard. The samples are incubated in the dark for 1-2 minutes before analyzing.

1% TRITON™ X-100 in TE buffer is then added to duplicate samples and RIBOGREEN® working solution is then added.

Encapsulation efficiency is determined from the fluorescent measurements using the average of the fluorescence results from each sample, corrected for baseline measurements of the average of external samples (fluorescence of RIBOGREEN® reagent in the absence of RNA), and after correcting for an 8% reduction in signal intensity due to the presence of TRITON™ X-100. Encapsulation efficiency is then calculated using the following equation:

$$EE=(TRITON™\ sample-liposome\ sample)/(TRITON™\ sample)$$

That is, encapsulation efficiency is the difference between the total RNA value (measured after dissolving the liposome with detergent) and the intact liposome value, divided by the total RNA value. The fluorescence obtained from the intact liposome sample will consist of free RNA in solution plus the RNA absorbed on the outside surface of liposome.

Size

Size indicates the size (diameter) of the particles formed. Size distribution may be determined using a Malvern Zetasizer Nano-ZS dynamic light scattering (DLS) instrument.

This procedure applies to the measurement of the volume mean diameter, Z-average diameter, and polydispersity for in-process liposome samples. Polydispersity is a numerical value for particle size distribution.

Measurements are performed at room temperature. Samples and reagents should be equilibrated to room temperature. The volume-weighted mean particle diameter and polydispersity index is determined.

Method of Manufacture

Preparation of Liposomes

The lipid mixture can be solubilized in a water miscible organic solvent, preferably absolute ethanol. In most embodiments, the organic solvent is used in the form in which it is commercially available.

In one exemplary embodiment, the mixture of lipids is a mixture of cationic amino lipids, neutral lipids (other than an amino lipid), a steroid (e.g., cholesterol), and a PEG-modified lipid (e.g., a PEG-S-DMG, PEG-C-DOMG or PEGDMA) are co-solubilized in the organic solvent. In preferred embodiments, the lipid mixture consists essentially of a cationic amino lipid, a neutral lipid, cholesterol and a PEG-modified lipid. In further preferred embodiments, the lipid mixture consists of a cationic lipid, DOPE (or another helper lipid, with either an ionizable or a permanent cationic charge), cholesterol and PEG-conjugated lipid at various molar ratios. Preferred molar ranges are between 40 to 60 mole % cationic lipid, 10 to 30% neutral lipid, 20 to 40% cholesterol, and 1 to 10% PEG-modified lipid.

A targeting lipid can be added to the lipid mixture, e.g., diVA-PEG750-diVA (or other VA-conjugated targeting lipid) at molar ratio of 0.1 to 5 (targeting lipid:total lipid).

The total concentration of lipid is less than 25 mg/ml, preferably less than 5 mg/ml. The lipid mixture is filtered through membrane, e.g. a 0.45 or 0.2 µm filter.

In accordance with the invention, the lipid mixture is combined with a buffered aqueous solution. The buffered aqueous solution may be a solution in which the buffer has a pH less than the pKa of a protonated lipid in the lipid mixture. Examples of suitable buffers include citrate, phosphate, and acetate. A particularly preferred buffer is citrate buffer. Preferred buffers will be in the concentration range of 1-1000 mM of the anion, depending on the chemistry of the nucleic acid being encapsulated, and optimization of buffer concentration may be significant to achieving high loading levels. It may be suitable to add a cryoprotectant, and/or a non-ionic solute, which will balance the osmotic potential across the particle membrane, e.g., when the particles are dialyzed to remove ethanol, increase the pH, or mixed with a pharmaceutically acceptable carrier or diluent. The amount of nucleic acid in buffer is from about 0.08 to 0.8 mg/mL.

At the time of addition of ethanol, the temperature of the aqueous solution is 25 to 45° C., preferably 30 to 40° C. The ethanol solution is added to the aqueous solution either by spraying on the air-water interface, in a narrow stream, or through a liquid-liquid interface between ethanol delivered through a tube that is submerged in the aqueous solution.

The organic solution is added by gravity or by a pump delivering the organic solution to the aqueous solution at a controlled rate, preferably a constant rate. The delivery of the organic solution can be completed in 1 minute to 100 minutes, preferably in 1 to 25 minutes. The organic solution may be added through a single spray or stream, through a tube or nozzle, or through a multi-nozzle system. While the organic solution is added into the aqueous solution, the resulting solution may be mixed by stirring, shaking, or recirculation. The addition step results in a final concentration that is preferably 25 to 45% ethanol, most preferably 35% ethanol.

The final solution is treated to remove the organic solvent, by dialysis or filtration, preferably by diafiltration. While the ethanol is removed, the aqueous solution is converted to a one buffered at a neutral pH, pH 6.8 to pH 7.5, preferably, pH 7.2, for example, a phosphate or HEPES buffer. The resulting aqueous solution is preferably sterilized before storage or use, e.g., by filtration through a 0.22 μm filter.

Liposomes Encapsulating Negatively Charged Therapeutic Polymers

The methods described herein are useful for preparing lipid particles with a negatively charged therapeutic polymer, e.g., an RNA molecule. In the methods described herein, a mixture of lipids is combined with an aqueous solution of the polymer. The polymer is efficiently encapsulated in the resulting lipid particles.

The nanoparticles may include a polyanionic active agent or therapeutic agent, e.g., an RNA and one, two or three biocompatible polymers. Exemplary therapeutic agents include nucleic acids, antineoplastic agents such as taxanes.

The total charge of the negatively charged polymer must be less than or equal to the number of positive charges in the lipid mixture at the time of addition is preferably 0.06 to 0.16 (w:w). For example, when RNA is used, the encapsulated nucleic acids are present in a final ratio of RNA:lipid 0.06 to 0.16, charge:charge (−/+), preferably 1:2.5 to 1:1.

When the mixture of lipids comprises a cationic lipid with a charge, lipid vesicles may be formed in the presence of negatively charged polymer to encapsulate and entrap the polymer. The resulting particles can be neutralized by increasing the pH of the medium to physiological pH or higher. The vesicles formed in this manner provide formulations of uniform vesicle size with high content of nucleic acids.

In either instance, the vesicles encapsulating the polymer (nanoparticles) have a size range of from 50 to 150 nm.

In accordance with the method described herein, the lipid mixture is combined with a buffered aqueous solution that may contain the negatively charged polymer. The buffered aqueous solution of may be a solution in which the buffer has a pH of less than the pKa of a protonated lipid in the lipid mixture. Examples of suitable buffers include citrate, phosphate, acetate, and MES. A particularly preferred buffer is citrate buffer. Preferred buffers will be in the range of 1-1000 mM of the anion, depending on the chemistry of the polymer being encapsulated, and optimization of buffer concentration may be significant to achieving high loading levels.

It may be suitable to add a cryoprotectant and/or a non-ionic solute which will balance the osmotic potential across the particle membrane when the particles are dialyzed to remove ethanol, increase the pH, or mixed with a pharmaceutically acceptable carrier and/or diluent.

For RNA, a schematic of the process described herein is depicted in FIG. 1. Solutions are prepared by dissolution of lyophilized or solid material in water, preferably buffered at pH 3.5-4.5, for example with 50 mM citrate. The amount of nucleic acid in buffer is from 0.08 to 0.8 mg/mL. At the time of addition of ethanol, the temperature of the aqueous solution is 25 to 45° C., preferably 30 to 40° C. If single stranded nucleic acid is used, briefly heating at elevated temperature may be useful, e.g., 1-2 minutes at 65° C.

The ethanol solution is added to the aqueous solution either by spraying on the air-water interface, in a narrow stream, or through a liquid-liquid interface between ethanol delivered through a tube that is connected to a container with the aqueous solution.

The organic solution is added by delivering the organic solution to the aqueous solution at a controlled rate, preferably at a constant rate. The delivery of the organic solution can be completed in 1 minute to 100 minutes, preferably in 1 to 25 minutes. The organic solution may be added through a single spray or stream, through a tube or nozzle, or through a multinozzle system. While the organic solution is added into the aqueous solution, the resulting solution it may be mixed by stirring, shaking, or recirculation. The addition step results in a final concentration sufficient to disrupt the liposomal bilayer structure, preferably 25 to 45% ethanol, most preferably 35% ethanol.

For lipid-nucleic acid particles, the final RNA concentration is 0.001 to 1 mg/ml, preferably 0.01 to 0.5 mg/ml, most preferably 0.05 to 0.5 mg/ml. The final drug/lipid ratio, is 0.06 to 0.16 w:w (2.5:1 to 1:1, charge:charge ratio).

The final solution is treated to remove the organic solvent, by dialysis or filtration, preferably by diafiltration. While the ethanol is removed, the aqueous solution is converted to a one buffered at a neutral pH, pH 6.8 to pH 7.5, preferably, pH 7.2, for example a phosphate buffer. The resulting aqueous solution is preferably sterilized before storage or use, e.g., by filtration through a 0.22 μm filter.

The final encapsulation efficiency is greater than 85%. The final mean particle diameter is 50 to 150 nm. The polydispersity index PDI is less than 0.2, preferably less than 0.1.

Lyophilization

The present disclosure relates in part to a lyophilized pharmaceutical composition that, when reconstituted, has a minimal amount of large aggregates. Such large aggregates may have a size greater than about 0.2 μm, greater than about 0.5 μm, or greater than about 1 μm, and can be undesirable in a reconstituted solution. Aggregate sizes can be measured using a variety of techniques including those indicated in the U.S. Pharmacopeia 32<788>, hereby incorporated by reference. The tests may include a light obscuration particle count test, microscopic particle count test, laser diffraction, and single particle optical sensing. In one embodiment, the particle size in a given sample is measured using laser diffraction and/or single particle optical sensing. DLS may be used to measure particle size, but it relies on Brownian motion so the technique may not detect some larger particles. Laser diffraction relies on differences in the index of refraction between the particle and the suspension media. The technique is capable of detecting particles at the sub-micron to millimeter range. Relatively small (e.g., about 1-5 wt %) amounts of larger particles can be determined in nanoparticle suspensions. Single particle optical sensing (SPOS) uses light obscuration of dilute suspensions to count individual particles of about 0.5 pm. By knowing the particle concentration of the measured sample, the weight percentage of aggregates or the aggregate concentration (particles/mL) can be calculated.

Formation of aggregates can occur during the freezing and/or drying steps of lyophilization, e.g., due to the dehydration of the surface of the particles. The freezing process has a concentrating effect that can reduce the distance between the particles as the ice forms (Alison et al., Biochim Biophys Acta. 2000 Sep. 29; 1468(1-2):127-38; Armstrong and Anchordoquy, J Pharm Sci. 2004 November; 93(11): 2698-709). This dehydration can be avoided by using lyoprotectants, such as polysaccharides, in the suspension before lyophilization. Suitable polysaccharides include sucrose, lactulose, lactose, maltose, trehalose, or cellobiose, kojibiose, nigerose, isomaltose, trehalose, sophorose, laminaribiose, gentiobiose, turanose, maltulose, palatinose, gentiobiulose, mannobiase, melibiose, melibiulose, rutinose, rutinulose, and xylobiose. In one embodiment, the composition comprises a polysaccharide that is sucrose. In another embodiment, the composition comprises a polysaccharide that is trehalose. Applicants results show, when compared to the starting suspension, that equivalent DLS size distributions are obtained upon reconstitution.

It was previously thought that vitrification, the process of immobilizing macromolecules in a glassy excipient, was not a contributing factor in preventing aggregation of liposomes and that hypertonic solutions of sugar were required (Alison et al.). The present inventors found that the results of the freezing and drying steps of lyophilization depend on a certain lipid:polysaccharide ratio (w:w), which provides a means to prevent that aggregation of liposomes, disruption of the liposomal diffusion barrier, and release of encapsulated RNA to form nucleic acid lipoplexes. In one embodiment, the composition comprises 12 to 15% (w:w) sucrose and 5 to 20 mg/ml lipid, preferably 12% sucrose and 9 mg/ml lipid. More preferably, the composition also comprises a buffer, most preferably HEPES at a neutral pH.

Lyophilization steps are carried out in a suitable glass receptacle, preferably a 10 ml, cylindrical glass vial. The glass vial must withstanding extreme changes in temperatures of less than −40° C. and greater than room temperature in short periods of time, and be cut in a uniform shape. The composition comprising the bulking agent and liposomes encapsulating nucleic acid is added to the vial, preferably in a 3 ml volume, and preferably with 9 mg/ml lipid.

The step of lyophilizing may comprise freezing the composition at a temperature of greater than about −40° C., or e.g. less than about −30° C., forming a frozen composition; and drying the frozen composition to form the lyophilized composition. The freezing step preferably results in a linear decrease in temperature to the final over about 6 minutes, preferably at 1° C./minute from 20 to −40° C. More preferably, sucrose at 12-15% may be used, and the drying step is at about 50-150 mTorr, first at a low temperature of about −15 to about −35° C., and thereafter at a higher temperature of room temperature to about 25° C., and is completed in three to seven days. In another embodiment of the present disclosure, trehalose may be used, and the drying step is at about 50-100 mTorr, first at a low temperature of about 0 to about −15° C., and then at the higher temperature.

In another aspect, the invention provides a method of preventing substantial aggregation of particles in a pharmaceutical nanoparticle composition comprising adding a sugar and a salt to the lyophilized formulation to prevent aggregation and release of nucleic acid from the interior of the liposome.

Pharmaceutical Compositions

The lipid particles disclosed herein, particularly when associated with a therapeutic agent, may be formulated as a pharmaceutical composition, e.g., which further comprises a pharmaceutically acceptable diluent, excipient, or carrier, such as physiological saline or phosphate buffer, selected in accordance with the route of administration and standard pharmaceutical practice. As would be appreciated by one of skill in this art, the carriers may be chosen based on the route of administration as described below, the location of the target issue, the drug being delivered, the time course of delivery of the drug, etc.

The pharmaceutical compositions of this invention can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles of the present invention are administered to a subject in need thereof systemically, e.g., parenterally, or by intravenous infusion or injection.

In particular embodiments, pharmaceutical compositions comprising the lipid-nucleic acid particles of the invention are prepared according to standard techniques and further comprise a pharmaceutically acceptable carrier. Generally, saline will be employed as the pharmaceutically acceptable carrier. Other suitable carriers include, e.g., water, buffered water, 0.9% saline, 0.3% glycine, a sugar or polysaccharide, e.g., sucrose, maltose, trehalose, a carrageenan, a xantham gum, mannitol, a fructan (e.g., inulin), a cyclodextrin, xylitol, sorbitol, or a polyethylene glycol (PEG), including glycoproteins for enhanced stability, such as albumin, lipoprotein, globulin. Bulking agents, cryo-protectants and/or lyoprotectants, as well as metal scavengers, e.g., EDTA, may be included. In compositions comprising saline or other salt containing carriers, the carrier is preferably added following lipid particle formation. Thus, after the lipid-nucleic acid compositions are formed, the compositions can be diluted into pharmaceutically acceptable carriers such as normal saline.

The resulting pharmaceutical preparations may be sterilized by conventional, well known sterilization techniques. The aqueous solutions can then be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, for example, sodium acetate, sodium lactate, sodium chloride, potassium chloride, or calcium chloride. Additionally, the lipidic suspension may include lipid-protective agents which protect lipids against free-radical and lipid peroxidative damages on storage. Lipophilic free-radical quenchers, such as a-tocopherol and water-soluble iron-specific chelators, such as ferrioxamine, are suitable.

The concentration of lipid particle or lipid-nucleic acid particle in the pharmaceutical formulations can vary widely, i.e., from less than about 0.01%, usually at or at least about 0.05-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, complexes composed of irritating lipids may be diluted to low concentrations to lessen inflammation at the site of administration. In one group of embodiments, the nucleic acid will have an attached label and will be used for diagnosis (by indicating the presence of complementary nucleic acid). In this instance, the amount of complexes administered will depend upon the particular label used, the disease state being diagnosed and the judgment of the clinician but will generally be between about 0.01 and about 50 mg per kilogram of body weight, preferably between about 0.001 and about 5 mg/kg of body weight.

Method of Use

The lipid particles described herein may be used to deliver a negatively charged therapeutic polymer, such as a nucleic acid to a cell, in vitro or in vivo. While the following description of various methods of using the lipid particles and related pharmaceutical compositions of the present invention are exemplified by description related to nucleic acid-lipid particles, it is understood that these methods and compositions may be readily adapted for the delivery of any therapeutic agent for the treatment of any disease or disorder that would benefit from such treatment.

In certain embodiments, the present invention provides methods for introducing a nucleic acid into a cell. Preferred nucleic acids for introduction into cells are siRNA, immune-stimulating oligonucleotides, plasmids, antisense and ribozymes. These methods may be carried out by contacting the particles or compositions of the present invention with the cells for a period of time sufficient for intracellular delivery to occur.

The compositions of the present invention can be adsorbed to almost any cell type. Once adsorbed, the nucleic acid-lipid particles can either be endocytosed by a portion of the cells, exchange lipids with cell membranes, or fuse with the cells. Transfer or incorporation of the nucleic acid portion of the complex can take place via any one of these pathways. Without intending to be limited with respect to the scope of the invention, it is believed that in the case of particles taken up into the cell by endocytosis the particles then interact with the endosomal membrane, resulting in destabilization of the endosomal membrane, possibly by the formation of nonbilayer phases, resulting in introduction of the encapsulated nucleic acid into the cell cytoplasm. Similarly in the case of direct fusion of the particles with the cell plasma membrane, when fusion takes place, the liposome membrane is integrated into the cell membrane and the contents of the liposome combine with the intracellular fluid. Contact between the cells and the lipid-nucleic acid compositions, when carried out in vitro, will take place in a biologically compatible medium. The concentration of compositions can vary widely depending on the particular application, but is generally between 1 μmol and 10 mmol. In certain embodiments, treatment of the cells with the lipid-nucleic acid compositions will generally be carried out at physiological temperatures (37° C.) for periods of time from 1 to 24 hours, preferably from 2 to 8 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

In one group of embodiments, a lipid-nucleic acid particle suspension is added to 60-80% confluent plated cells having a cell density of from about $10^3$ to about $10^5$ cells/mL, more preferably about $2 \times 10^4$ cells/mL. The concentration of the suspension added to the cells is preferably of from about 0.01 to 20 μg/mL, more preferably about 1 μg/mL.

Typical applications include using well known procedures to provide intracellular delivery of siRNA to knock down or silence specific cellular targets. Alternatively applications include delivery of DNA or mRNA sequences that code for therapeutically useful polypeptides.

Methods of the present invention may be practiced in vitro, ex vivo, or in vivo. For example, the compositions of the present invention can also be used for delivery of nucleic acids to cells in vivo, using methods which are known to those of skill in the art.

For in vivo administration, the pharmaceutical compositions are preferably administered parenterally, i.e., intraarticularly, intravenously, intraperitoneally, subcutaneously, or intramuscularly. In particular embodiments, the pharmaceutical compositions are administered intravenously or intraperitoneally by a bolus injection.

In other methods, the pharmaceutical preparations may be contacted with the target tissue by direct application of the preparation to the tissue. The application may be made by topical, "open" or "closed" procedures. By "topical," it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The lipid-nucleic acid compositions can also be administered in an aerosol inhaled into the lungs or by direct injection at the site of disease.

The methods of the present invention may be practiced in a variety of subjects or hosts. Preferred subjects or hosts include mammalian species, such as humans, non-human primates, dogs, cats, cattle, horses, sheep, and the like. In particular embodiments, the subject is a mammal, such as a human, in need of treatment or prevention of a disease or disorder, e.g., a subject diagnosed with or considered at risk for a disease or disorder.

Dosages for the lipid-therapeutic agent particles of the present invention will depend on the ratio of therapeutic agent to lipid and the administrating physician's opinion based on age, weight, and condition of the patient.

In one embodiment, the present invention provides a method of modulating the expression of a target polynucleotide or polypeptide. These methods generally comprise contacting a cell with a lipid particle of the present invention that is associated with a nucleic acid capable of modulating the expression of a target polynucleotide or polypeptide. As used herein, the term "modulating" refers to altering the expression of a target polynucleotide or polypeptide. In different embodiments, modulating can mean increasing or enhancing, or it can mean decreasing or reducing. Methods of measuring the level of expression of a target polynucleotide or polypeptide are known and available in the arts and include, e.g., methods employing reverse transcription-polymerase chain reaction (RT-PCR) and immunohistochemical techniques. In particular embodiments, the level of expression of a target polynucleotide or polypeptide is increased or reduced by at least 10%, 20%, 30%, 40%, 50%, or greater than 50% as compared to an appropriate control value.

For example, if increased expression of a polypeptide desired, the nucleic acid may be an expression vector that includes a polynucleotide that encodes the desired polypeptide. On the other hand, if reduced expression of a polynucleotide or polypeptide is desired, then the nucleic acid may be, e.g., an antisense oligonucleotide, siRNA, or microRNA that comprises a polynucleotide sequence that specifically hybridizes to a polynucleotide that encodes the target polypeptide, thereby disrupting expression of the target polynucleotide or polypeptide. Alternatively, the nucleic acid may be a plasmid that expresses such an antisense oligonucleotide, siRNA, or microRNA.

In particular embodiments, the nucleic acid active agent or therapeutic agent is selected from an siRNA, a microRNA, an antisense oligonucleotide, and a plasmid capable of expressing an siRNA, a microRNA, or an antisense oligonucleotide, and in which the siRNA, microRNA, or antisense RNA comprises an oligonucleotide that specifically binds to a polynucleotide that encodes the polypeptide, or a complement thereof, such that the expression of the polypeptide is reduced.

In other embodiments, the nucleic acid is a plasmid that encodes the polypeptide or a functional variant or fragment thereof, such that expression of the polypeptide or the functional variant or fragment thereof is increased.

In related embodiments, the present invention provides a method of treating a disease or disorder characterized by overexpression of a polypeptide in a subject, comprising providing to the subject a pharmaceutical composition of the present invention, in which the therapeutic agent is selected from an siRNA, a microRNA, an antisense oligonucleotide, and a plasmid capable of expressing an siRNA, a microRNA, or an antisense oligonucleotide, and in which the siRNA, microRNA, or antisense RNA comprises an oligonucleotide that specifically binds to a polynucleotide that encodes the polypeptide, or a complement thereof.

In another related embodiment, the present invention includes a method of treating a disease or disorder characterized by under-expression of a polypeptide in a subject, comprising providing to the subject a pharmaceutical composition of the present invention, in which the therapeutic agent is a plasmid that encodes the polypeptide or a functional variant or fragment thereof.

Assaying Shelf Life

The term "shelf life" is used herein to refer to the period of time the lipid:RNA nanoparticles can be stored (under defined conditions e.g., in a buffer at 4° C.) before losing its biological activity. The biological activity assayed for determination of shelf life in the present invention is the ability of the lipid:RNA nanoparticles to transfect mammalian cells in vivo after intravenous administration.

In a preferred embodiment the shelf life is determined by storing the lipid:RNA nanoparticles for varying periods of time, injecting one or more test animals with the nanoparticles and assaying selected tissues in the animal for transfection (e.g., expression of a reporter gene) as described above and as illustrated in the examples.

It will be appreciated that shelf life can be expressed in absolute terms, i.e., the length of time the composition can be stored before losing activity. Alternatively, shelf life can be expressed in relative terms by reference to a different composition. Thus, for example, when the lipid:RNA nanoparticles shows transfection activity after a fixed period of storage and this activity is greater than the activity of a different complex similarly stored for the same amount of time, the subject complex is said to have an increased shelf life as compared to the different complex.

Kits Comprising Liposome-Encapsulated Polyanionic Therapeutic

The present invention also provides for kits for preparing the lipid:RNA nanoparticles described herein. Such kits can be prepared from readily available materials and reagents, as described above. For example, such kits can comprise any one or more of the following materials: liposomes, nucleic acid (RNA, DNA, single or double-stranded), hydrophilic polymers, hydrophilic polymers derivatized with targeting moieties such as Fab' fragments, and instructions. A wide variety of kits and components can be prepared according to the present description, depending upon the intended user of the kit and the particular needs of the user. For example, the kit may contain any one of a number of targeting moieties for targeting the complex to a specific cell type, as described above.

The kit may optionally include instructional materials containing directions (i.e., protocols) providing for the use of the lipid:RNA nanoparticles for transfecting cells in vivo, ex vivo, or in vitro. Typically, the instruction materials describe the procedure for preparing the lipid:RNA nanoparticles from liposomes and nucleic acid, as described above. The instruction materials also describe how to mix the hydrophilic polymer with the lipid:RNA nanoparticles. Additionally, the instruction materials can describe procedures for transfecting cells with the lipid:RNA nanoparticles.

EXAMPLES

Example 1: Effect of Concentration on RNA-Lipid Particle Size

This example describes the effect of siRNA and lipid concentration on particle size.

To prepare nanoparticles by the method described herein. A cationic lipid, DOPE, cholesterol, a PEG-BML, and diVA-PEG750-diVA were solubilized in absolute ethanol at a molar ratio of 50:10:38:2:5, respectively. The siRNA was solubilized in 50 mM citrate buffer at pH 4.5.

A siRNA-containing buffer was brought to 35 to 40° C. while continuously stirring in a mixing vessel. The ethanol/lipid mixture was then sprayed onto the surface of the siRNA containing buffer using a manifold/nozzle array to spontaneously form siRNA loaded liposomes. Lipid and RNA concentrations were adjusted to reach a final siRNA concentration range from 0.05 to 0.5 mg/mL, a drug:lipid ratio of 0.08 (wt:wt), and an ethanol concentration of 35%. The lipid to siRNA ratio was kept constant for all conditions tested.

Figure 2:
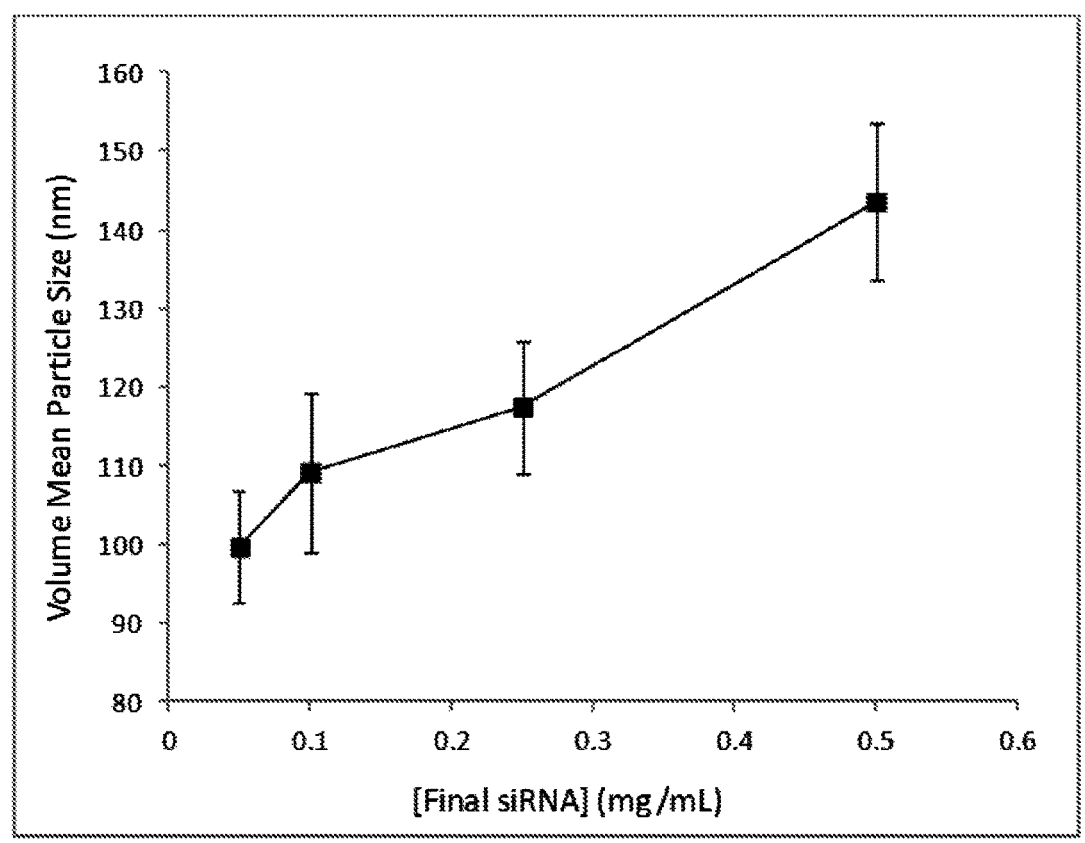
FIG. 2 shows the mean particle size in nanometers (nm) as a function of final RNA concentration, from 0.05 to 0.5 mg/mL. The experimental details are provided in Example 1.

The siRNA loaded liposomes were diluted to ~10% ethanol to stabilize the particles and then diafiltered against 10× volumes of PBS (pH 7.2) to remove ethanol and exchange the buffer. Final product was filtered through 0.22 μm, sterilizing grade, PES filter for bioburden reduction. Volume, mean particle size and PDI were determined using DLS. The results are shown in the Table I and FIG. 2.

TABLE 1

| Final | Vol. Mean Diam. [nm] | | |
|---|---|---|---|
| siRNA | Mean | SD | PDI |
| 0.05 | 96.7 | 7.0 | 0.084 |
| 0.10 | 105.7 | 10.1 | 0.073 |
| 0.25 | 116.8 | 8.4 | 0.125 |
| 0.50 | 141.9 | 10.0 | 0.105 |

The results show that particle size increases with increasing siRNA concentration (in mg/ml). Reducing the lipid and siRNA concentrations (keeping the same relative ratio) reduces particles size, while increasing concentration increases particle size. Final siRNA concentrations between 0.05 to 0.5 mg/ml produce nanoparticles with a mean particle diameter of 96.7 to 141.9 nm, less than 150 nm, and with a polydispersity index less than 0.2 in all cases.

Particles size less than 150 nm with a PDI less than 0.2 are produced by the method described herein, without preparing empty preformed lipid vesicles and/or without mechanical processing.

Example 2: Effect of Process Parameters on RNA-Lipid Particle Formation

This example describes the effect of various process parameters on RNA-Lipid particle formation. Several parameters were screened during this experiment, including temperature, ethanol concentration, buffer, lipid:siRNA ratio, and the nozzle type used to disperse the lipid solution.

HEDC, DOPE, cholesterol, a PEG-BML, and diVA-PEG750-diVA were dissolved in absolute ethanol of at a molar ratio of 40:30:25:5:2. The siRNA containing buffer was brought to the indicated temperature while continuously stirring in a mixing vessel. The ethanol/lipid mixture was then sprayed onto the surface of the siRNA containing buffer using a nozzle to spontaneously form siRNA loaded liposomes. Lipids were combined with siRNA to reach a final siRNA concentration of 0.1 mg/mL at the indicated drug/lipid ratio and the indicated the final ethanol percentage.

The siRNA was solubilized in citrate buffer that was varied in strength from 25 to 100 mM and pH 3.5 to pH 6.5. The mixture temperature was varied from 25 to 45° C. The final ethanol concentration varied from 25 to 45%. The drug:lipid ratio (wt/wt) varied from 0.07 to 0.11. The hydration nozzle inner diameter (ID) varied from 0.005 to 0.125 inches. Each condition was performed as a measurement to compare the effect of each process parameter. Unless indicated each condition was performed at with 50 mM citrate buffer, pH 4.5, 35° C., 35% final ethanol, drug:lipid ratio of 0.07, and nozzle ID of 0.005 inches.

The siRNA loaded liposomes were diluted to 10% ethanol to stabilize the particles and then diafiltered against 10× volumes of PBS (pH 7.2) to remove ethanol and exchange the buffer. Final product was filtered through 0.22 μm, sterilizing grade, PES filter for bioburden reduction.

Figure 3:
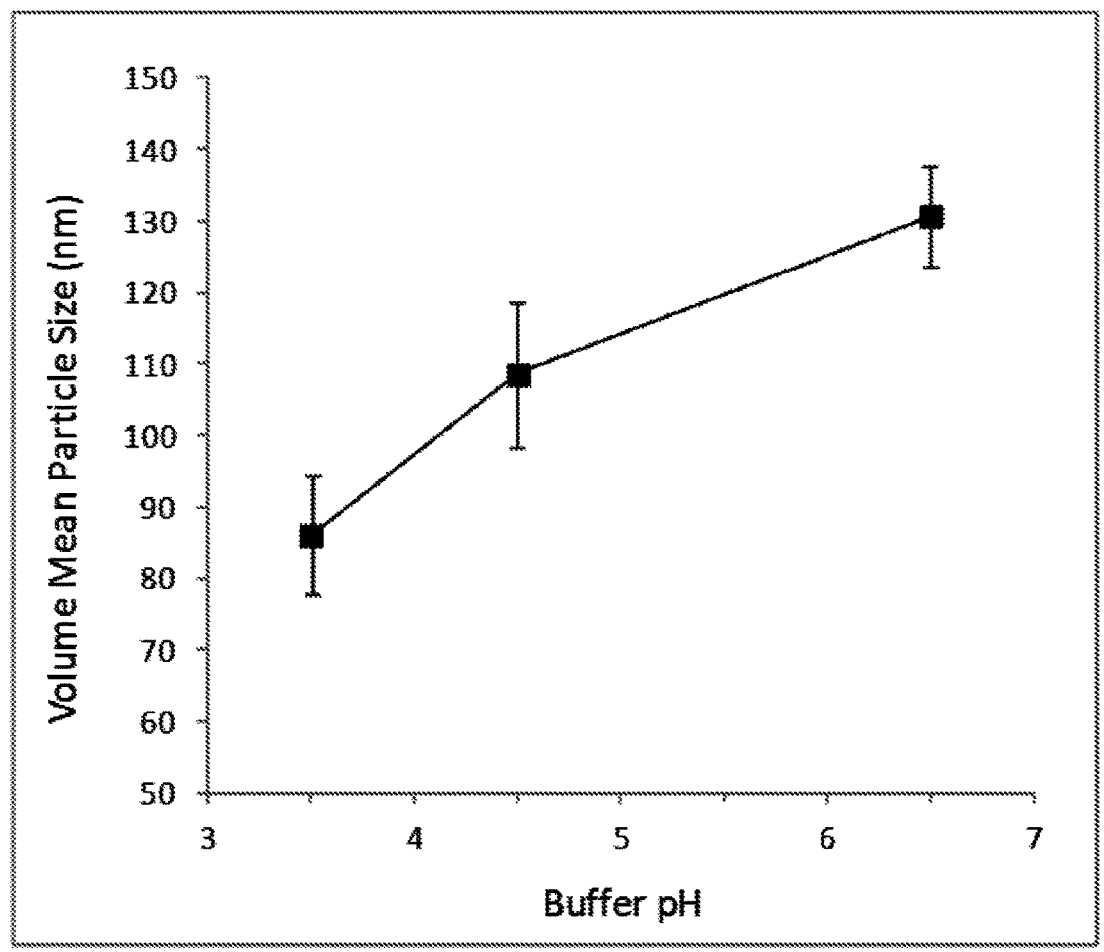
FIG. 3 shows the mean particle size in nm as a function of buffer pH while mixing the lipids to the RNA. The experimental details are provided in Example 2.

Table 2 and FIG. 3 show the effect of pH on the mean diameter and PDI of the lipid-nucleic acid nanoparticles. Increasing buffer pH resulted in increasing particle size, albeit less than 150 nm mean particle size.

TABLE 2

| Buffer pH | Vol. Mean Diam. [nm] | | |
|---|---|---|---|
| | Mean | SD | PDI |
| 6.5 | 130.7 | 17.7 | 0.111 |
| 4.5 | 108.5 | 7.1 | 0.163 |
| 3.5 | 86.1 | 10.2 | 0.149 |

Table 3 shows the effect of buffer concentration on various parameters. The results showed that increasing buffer concentration reduced siRNA recovery. The mean particle diameter and PDI appeared unaffected. Minimum particle size was observed for pH 3.5 and maximum siRNA recovery was observed for 25 mM citrate buffer.

TABLE 3

| Buffer Conc. [mM] | Vol. Mean Diam. [nm] | | | EE [%] | siRNA Recovery [%] |
|---|---|---|---|---|---|
| | Mean | SD | PDI | | |
| 25 | 103.1 | 13.4 | 0.179 | 96 | 94 |
| 50 | 113.8 | 15.5 | 0.156 | 94 | 87 |
| 100 | 101.0 | 9.4 | 0.185 | 94 | 80 |

Table 4 shows that increasing hydration temperature from 25 to 45° C. decreased particle size from 135.7 to 102.2 nm while improving siRNA recovery from 80% to 87%. Increasing final ethanol percentage increased particle size with no effect on siRNA recovery, but reduced encapsulation efficiency to 88%.

TABLE 4

| Hydration Temp [° C.] | Final % EtOH | Vol. Mean Diam. [nm] | | | EE [%] | siRNA Recovery [%] |
|---|---|---|---|---|---|---|
| | | Mean | SD | PDI | | |
| 25 | 35 | 135.7 | 15.9 | 0.057 | 95 | 80 |
| 35 | 25 | 103.8 | 9.8 | 0.178 | 94 | 84 |
| 35 | 35 | 113.8 | 15.5 | 0.156 | 94 | 87 |
| 35 | 45 | 130.8 | 11.7 | 0.136 | 88 | 86 |
| 45 | 35 | 102.2 | 3.4 | 0.182 | 93 | 87 |

Table 5 shows that increasing the drug:lipid ratio decreased, siRNA recovery increased from 80 to 87%. Maximum recovery was observed at a ratio of 0.07 drug:lipid (w:w). All other measured properties were unaffected by drug:lipid ratio. This result is surprising and unexpected in view of the disclosure of Maurer et al. and Semple et al., who both describe optimal recovery is at drug:lipid (w:w) equal to or greater than 0.16 (lipid:drug (w:w) equal to or less than 6.25). The current results suggest an opposite trend is obtained using the method described herein.

TABLE 5

| Lipid:siRNA [wt/wt] | Vol. Mean Diam. [nm] | | | EE [%] | siRNA Recovery |
|---|---|---|---|---|---|
| | Mean | SD | PDI | | |
| 9:1 | 93.9 | 17.6 | 0.186 | 95 | 80 |
| 12:1 | 85.6 | 14.0 | 0.218 | 95 | 82 |
| 14:1 | 113.8 | 15.5 | 0.156 | 94 | 87 |

Table 6 shows that increasing nozzle ID by 25 times did not impact particle size, encapsulation efficiency or siRNA recovery. There is substantial flexibility in the nozzle orifice being used to add the ethanol/lipids to the buffer surface. This flexibility could provide a major advantage during scale up.

TABLE 6

| Nozzle ID [inch] | Vol. Mean Diam. [nm] | | | EE [%] | siRNA Recovery |
|---|---|---|---|---|---|
| | Mean | SD | PDI | | |
| 0.005 | 105.2 | 5.8 | 0.119 | 98 | 81 |
| 0.050 | 100.7 | 11.7 | 0.124 | 96 | 87 |
| 0.125 | 109.7 | 13.3 | 0.097 | 96 | 81 |

Example 3: Comparison of Described Process to Referenced Methods for Batch Production of Liposomes These results compared the process described herein for preparing lipid/nucleic acid particles to the method described by Semple, et al. U.S. Pat. No. 6,858,225 (control method or control composition used by the control method). were prepared according to the composition of Example 2 or using the control method.

The composition of Example 2 consisted of a cationic lipid, DOPE, cholesterol, PEG conjugated lipid, and targeting lipid co-solubilized at a molar ratio of 40:30:25:5:2 (see Example 2, above).

The control composition consisted of DODAP, DSPC, cholesterol, and PEG-CER-14, co-solubilized at a molar ratio of 25:20:45:10.

In the method of Example 2, lipids were solubilized at 4.32 mg/ml in absolute ethanol, and siRNA was solubilized at 0.163 mg/ml in 50 mM citrate, pH 4.5. The siRNA solution was brought to 35 to 40° C. while continuously stirring in a mixing vessel. The ethanol/lipid mixture was then sprayed onto the surface of the siRNA containing buffer using a manifold/nozzle array. The final ethanol concentration was 35% and the final lipid/siRNA ratio was 14:1 (wt:wt). The resulting particles were then diluted to 10% ethanol and then diafiltered against 10× volumes of PBS (pH 7.2).

In the control method, lipids were solubilized at 25 mg/ml in absolute ethanol, and siRNA was solubilized at 4.17 mg/ml in 300 mM citrate, pH 4.0. The siRNA containing buffer was kept at room temperature while continuously stirring in a mixing vessel. The ethanol/lipid mixture was then sprayed onto the surface of the siRNA containing buffer using a single nozzle to spontaneously form siRNA loaded liposomes. The final ethanol concentration was 40%, and the final lipid/siRNA ratio was 6:1 (wt:wt). After mixing, the lipid/siRNA suspension was transferred into a 10 mL extruder prepared with two, 100 nm polycarbonate membranes and pre-equilibrated at 65° C. The suspension was extruded using ten passes at 300 psi. The resulting particles were diafiltered against 10× volumes of PBS, pH 7.2.

The particles resulting from each method were passed through a 0.22 µm filter. Mean particle size, PDI, and EE were measured as described herein.

Figure 4:
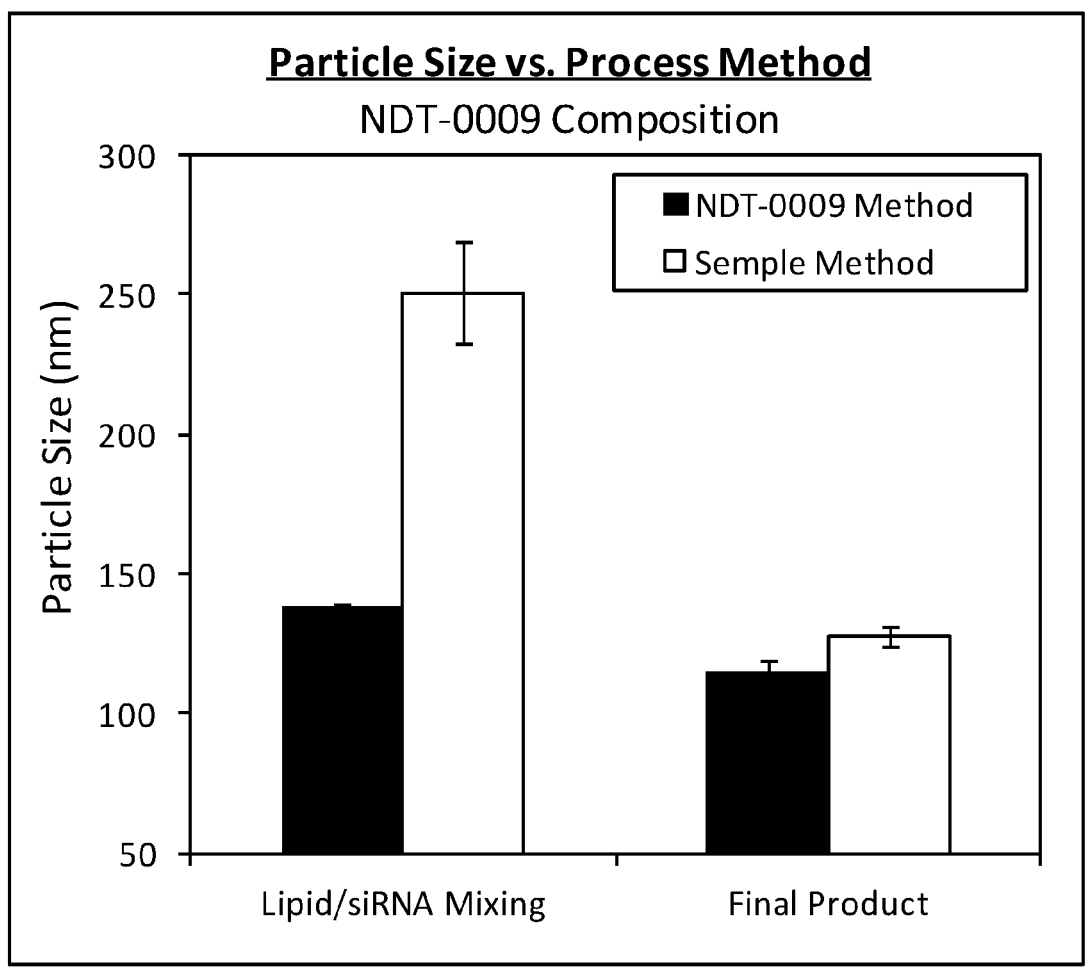
FIG. 4 shows the mean particle size of particles prepared using the method of Example 2 (NDT-0009) or the Semple method, as described in Example 3. The bars on the left are measurements of size after mixing. The bars on the right are measurements of the final product (for the product of the Semple method, after extrusion and diafiltration).

The Method of Example 2 produced smaller lipid nanoparticles than the control method without the extrusion step (FIG. 4). The size of the particles produced by the control method was measured before extrusion. Particles prepared from the NDT-0009 composition using the control method had a mean particle size of greater than 250 nm particles. After extrusion and diafiltration the mean particle size reduced to 128 nm. The Method of Example 2 produced particles with a mean particle size less than 150 nm without extrusion. A similar trend was observed starting with the control composition.

Figure 5:
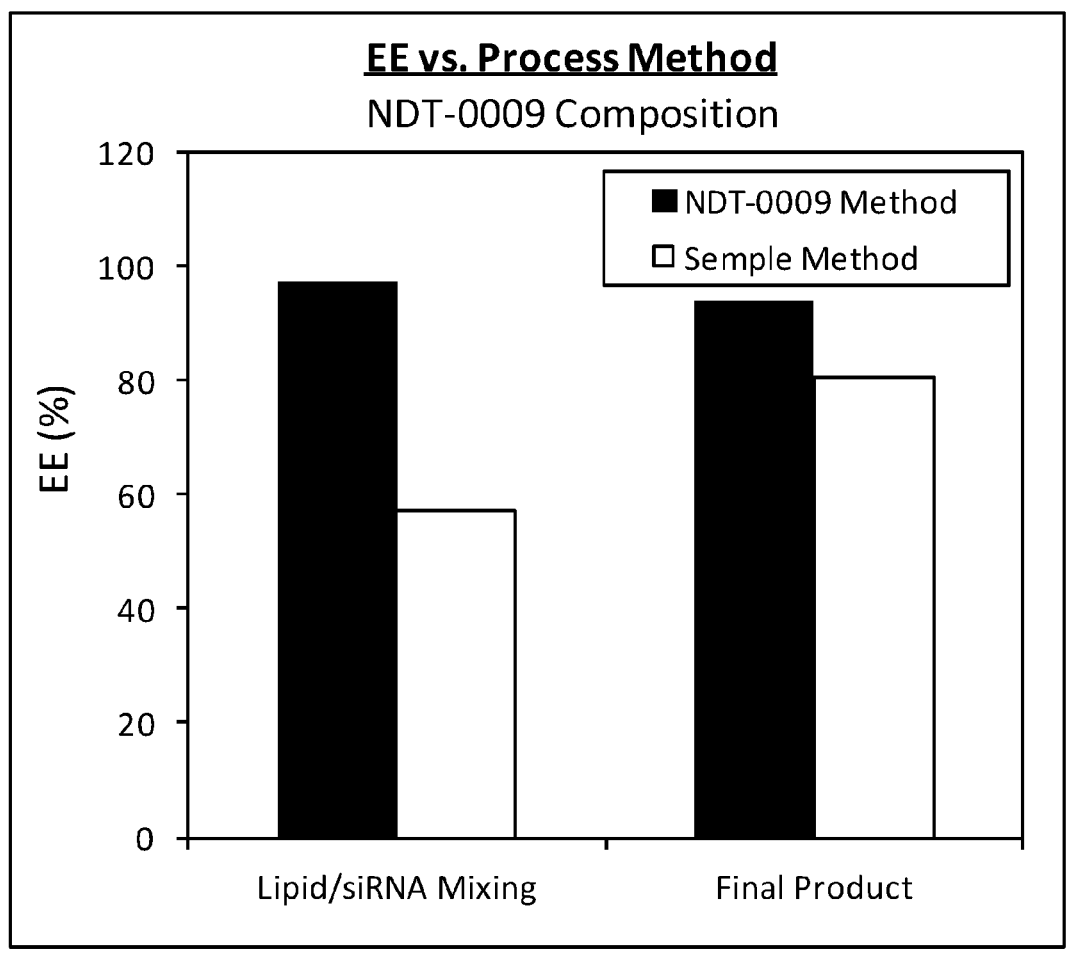
FIG. 5 shows the encapsulation efficiency (EE) in percentage, for the particle prepared using the method of Example 2 ("Method of Example 2") or the Semple method, as described in Example 3. The bars on the left are measurements of size after mixing. The bars on the right are measurements of the final product (for the product of the Semple method, after extrusion and diafiltration).

The Method of Example 2 was more efficient at encapsulating siRNA into the lipid nanoparticles than the control method (FIG. 5). The encapsulation efficiency (EE) of the particles prepared by the Method of Example 2 is higher than those of particles formed by the control method (measured prior to diafiltration in both products). The EE of particles prepared by the Method of Example 2 are greater than 95% higher than those found for particles formed by the control method. In the control method, much of the free siRNA is removed after diafiltration which results in an improvement in EE of the final product.

Figure 6:
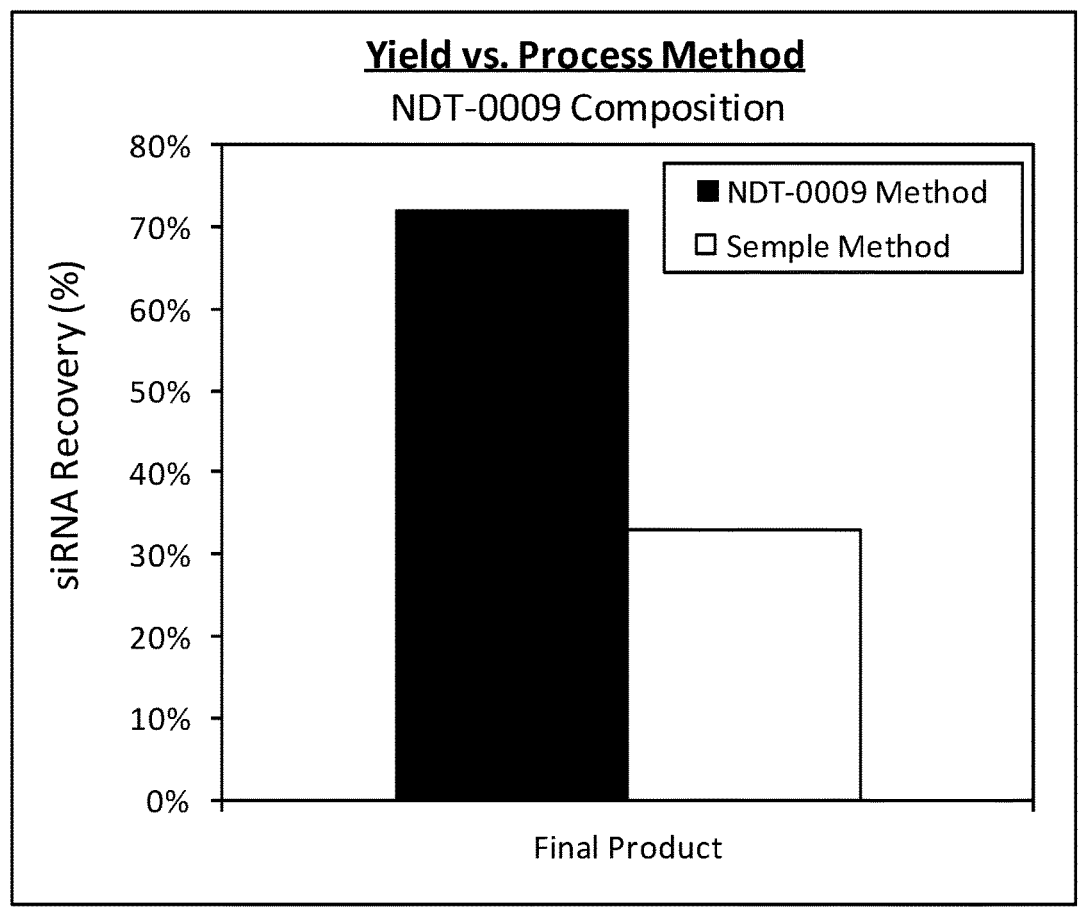
FIG. 6 shows the siRNA recovery, in percentage, for the particle prepared using the method of Example 2 or the Semple method, as described in Example 3.

The Method of Example 2 produces nanoparticles with higher encapsulation efficiency than the control method (FIG. 6). Final recovery of siRNA by the Method of Example 2 was more than twice that obtains by the control method (72% vs. 33%), as measured after diafiltration in both products. These data reflect the improvement in EE as well as the lack of an extrusion step in the Method of Example 2. The Method of Example 2 provides better siRNA recovery because the extra extrusion step of the control method structurally changes the liposomes, and apparently dissociates siRNA from the particles. These results show that the method described herein provides several advantages over the control method by reducing the number of process steps while improving encapsulation efficiency and yield of nanoparticles with a mean particle size less than 150 nm.

Example 4: Comparison of Variability During Scale-Up of Liposome Batch Production The process as described in Example 2 was performed with a different lipid composition that included the combination of a permanently charged (HEDC) cationic lipid and an ionizable (S104) cationic lipid molecule. HEDC, S104, DOPE, cholesterol, a PEG-BML, and diVA-PEG750-diVA were dissolved in absolute ethanol of at a molar ratio of 20:20:30:25:5:2. During scale-up different siRNA molecules, different batch volumes, and different siRNA (drug)/lipid ratios were evaluated. Table 7 summarizes the results of characterizing the nanoparticles resulting from the range of conditions.

TABLE 7

| Batch Vol [L] | Drug Substance | drug/lipid [wt/wt] | Particle size [nm] | PDI | EE [%] | Product Yield [siRNA recovery] |
|---|---|---|---|---|---|---|
| 5 | siRNA 1 | 0.07 | 93 | 0.14 | 97% | >90% |
| 20 | siRNA 1 | 0.07 | 83 | 0.15 | 95% | >90% |
| 20 | Empty Liposomes (no siRNA) | na | 83 | 0.14 | na | na |
| 20 | siRNA 2 | 0.11 | 90 | 0.16 | 92% | >90% |
| 50 | siRNA 2 | 0.07 | 82 | 0.14 | 94% | >90% |
| 120 | Empty Liposomes (no siRNA) | na | 86 | 0.14 | na | na |
| 120 | siRNA 2 | 0.11 | 82 | 0.14 | 94% | >90% |
| 200 | siRNA 1 | 0.07 | 86 | 0.17 | 94% | >90% |
| 200 | siRNA 2 | 0.07 | 86 | 0.17 | 96% | >90% |

The results show that the method described herein is quite robust. Similar particle size and PDI were obtained during a scale up spanning a 50-fold range. Particle size is consistently less than 100 nm, with >90% product yields. Polydispersity index values are in a very low range, indicating a nearly monodisperse population of vesicles.

Example 5: Comparison of Variability During Scale-Up of Liposome Batch Production for Sucrose Containing Formulations The process as described in Example 2 was performed with HEDC, 5104, DOPE, cholesterol, a PEG-BML, and diVA-PEG750-diVA dissolved in ethanol at a molar ratio of 20:20:30:25:5:2. Sucrose was included in the preparation of the vesicles as described herein. Different batch volumes were evaluated and subject to freeze-thawing. Table 8 summarizes the results of characterizing the nanoparticles resulting from a range of conditions.

TABLE 8

Frozen (sucrose containing) formulations prepared using semi Single-use manufacturing train

| Batch | | | Before Freezing | | | After Thawing | | | Product Yield |
|---|---|---|---|---|---|---|---|---|---|
| Vol [L] | Drug Substance | drug/lipid [wt/wt] | Size [nm] | PDI | EE [%] | Size [nm] | PDI | EE [%] | [siRNA recovery] |
| 5 | siRNA 2 | 0.11 | 94 | 0.12 | 95 | 96 | 0.14 | 93 | >90% |
| 20 | siRNA 2 | 0.11 | 98 | 0.15 | 94 | 97 | 0.16 | 90 | >90% |
| 120 | siRNA 2 | 0.11 | 96 | 0.14 | 90 | 96 | 0.14 | 89 | >90% |
| 120 | siRNA 2 | 0.11 | 97 | 0.15 | 91 | 99 | 0.15 | 89 | >90% |
| 120 | siRNA 2 | 0.11 | 100 | 0.15 | 91 | tbd | tbd | tbd | >90% |

The results show that freeze thawing did not change the properties of the lipid nanoparticles. The results also showed that variability between batches is quite low and that the process reproducibly produces uniform nanoparticles.

Conditions have been established for the stabilization of drug:lipid particles by lyophilization. Drug:lipid particles prepared according to the Method of Example 2 could be lyophilized without loss of activity. The final concentration of sucrose in which drug:lipid particles were formed was 8% (w/v). The lyophilized preparations were reconstituted by adding distilled water and their transfection activity in the lungs of mice after i.v. injection was measured. Freezing and thawing the reconstituted preparation did not affect the activity. The results shown in Table 9 demonstrate that particles prepared used the method described herein preserve their properties during lyophilization, and hence are stable. Specifically, particle size is stabilized and preserved before, during, and after lyophilization.

The stability of the particles is a function of the lipid composition, the lipid:RNA (w:w) values, and the choice of polysaccharide used in the formulation The methodical approach described herein for producing stable formulations of lipid:RNA complexes exhibiting high bioactivity in vivo confers advantages for establishing pharmaceutically acceptable preparations, and therefore facilitates liposome based RNA delivery.

Example 6: Submerged Injection of Lipid

The process as described in Example 2 was performed modified by preparing vesicles using submerged injection. HEDC, 5104, DOPE, cholesterol, a PEG-BML, and diVA-PEG750-diVA were dissolved in ethanol at a molar ratio of 20:20:30:25:5:2. Table 10 summarizes the results of characterizing the nanoparticles resulting from the submerged addition process compared to the surface addition process.

The results show the surprising and unexpected result that the mean particle size substantially decreases when the lipids are added to the aqueous phase by submerged injection.

TABLE 9

Lyo (sucrose containing) formulations prepared using semi Single-use manufacturing train

| Batch | | | Before Freezing | | | After Thawing | | | After Lyophilization + Reconstitution | | |
|---|---|---|---|---|---|---|---|---|---|---|---|
| Vol (L) | Drug Substance | drug/lipid [wt/wt] | Size [nm] | PDI | EE [%] | Size [nm] | PDI | EE [%] | Size [nm] | PDI | EE [%] |
| 20 | sIRNA 2 | 0.11 | 98 | 0.15 | 94 | 97 | 0.16 | 90 | 115 | 0.15 | 93 |

TABLE 10

| Batch | | | | Particle Size | | | Product Yield |
|---|---|---|---|---|---|---|---|
| Vol [L] | Drug Substance | drug/lipid [wt/wt] | Addition Method | Mean [nm] | PDI | EE [%] | [siRNA recovery] |
| Liquid Formulations prepared using semi Single-use manufacturing train | | | | | | | |
| 5 | siRNA 1 | 0.07 | Surface | 93 | 0.136 | 97 | >90% |
| 5 | siRNA 1 | 0.07 | Submerged | 57 | 0.104 | 97 | >90% |
| Frozen (sucrose containing) formulations prepared using semi Single-use manufacturing train | | | | | | | |
| 5 | siRNA 1 | 0.11 | Surface | 94 | 0.119 | 95 | >90% |
| 1 | siRNA 1 | 0.11 | Submerged | 63 | 0.102 | 95 | >90% |

The same process method was used to prepared liposomes containing sucrose in the buffer. Table 11 summarizes the results of characterizing the nanoparticles resulting from different addition times and Table 12 summarizes the results of characterizing nanoparticles prepared using surface compared to submerged addition.

TABLE 11

Liquid Formulations prepared using semi Single-use manufacturing train

| Addition Time [min] | Addition Method | Particle Size | | EE [%] | Product Yield [siRNA recovery] |
|---|---|---|---|---|---|
| | | Mean [nm] | PDI | | |
| 0.5 | Submerged | 66 | 0.140 | 90 | >90% |
| 2.0 | Submerged | 93 | 0.112 | 94 | >90% |
| 5.0 | Submerged | 99 | 0.133 | 92 | >90% |
| 10 | Submerged | 98 | 0.137 | 91 | >90% |

TABLE 12

Liquid Formulations prepared using semi Single-use manufacturing train

| Batch Vol [L] | Addition Time [min] | Addition Method | Particle Size | | EE [%] | Product Yield [siRNA recovery] |
|---|---|---|---|---|---|---|
| | | | Mean [nm] | PDI | | |
| 5 | 15 | Surface | 93 | 0.136 | 95 | >90% |
| 1 | 1.5 | Submerged | 63 | 0.102 | 95 | >90% |

The results show the surprising and unexpected result that the mean particle size substantially decreases when the lipids are added to the aqueous phase by submerged injection with an addition time of less than 2 minutes. The results also show the surprising results that mean particle size substantially decreases when the lipids are added to the aqueous phase by submerged injection.

What is claimed:

1. A method for preparing a population of lipid nanoparticles encapsulating a nucleic acid molecule, comprising the steps of
   (a) transferring to a mixing container an aqueous solution comprising a buffer and the nucleic acid molecule;
   (b) injecting a lipid solution comprising a cationic lipid, a helper lipid, a sterol, and a PEG lipid dissolved in a water-miscible organic solvent into the aqueous solution in the mixing container while stirring the aqueous solution;
   (c) diluting the organic solvent in the mixing container by adding an aqueous buffer to prevent aggregation of the lipid nanoparticles in a diluted mixture; and
   (d) removing the organic solvent from the diluted mixture to produce the population of lipid nanoparticles having a polydispersity index of less than 0.2 and an average size of 50 to 150 nm;
wherein step (b) is performed batchwise.

2. The method of claim of 1, wherein the aqueous solution further comprises a polysaccharide.

3. The method of claim 2, wherein the polysaccharide consists of sucrose, trehalose, mannitol, sorbitol, xylitol, lactose, maltose, or inulin.

4. The method of claim of 1, further comprising the step of lyophilizing the population of lipid nanoparticles.

5. The method of claim 1, wherein the water-miscible organic solvent is ethanol.

6. The method of claim 1, wherein the population of lipid nanoparticles has a nucleic acid:lipid ratio 0.06 to 0.16 (w:w), and a nucleic acid:lipid charge ratio of 1:2.5 to 1:1, and the cationic lipid is 40 to 60 mole percent of the lipids.

7. The method of claim 1, wherein the cationic lipid is selected from the group consisting of

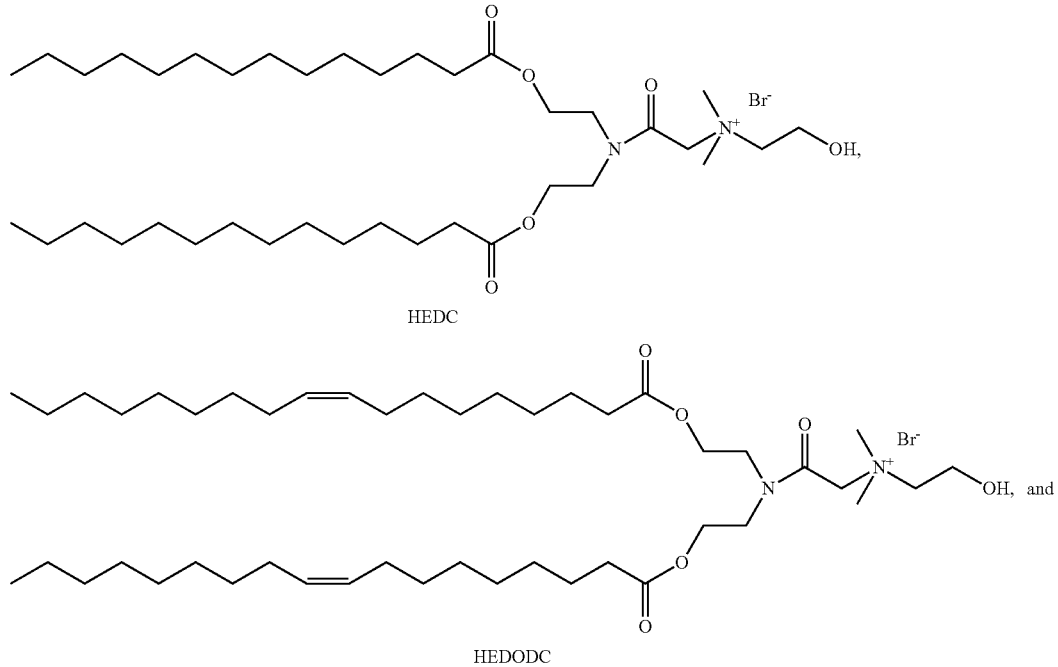

HEDC

HEDODC

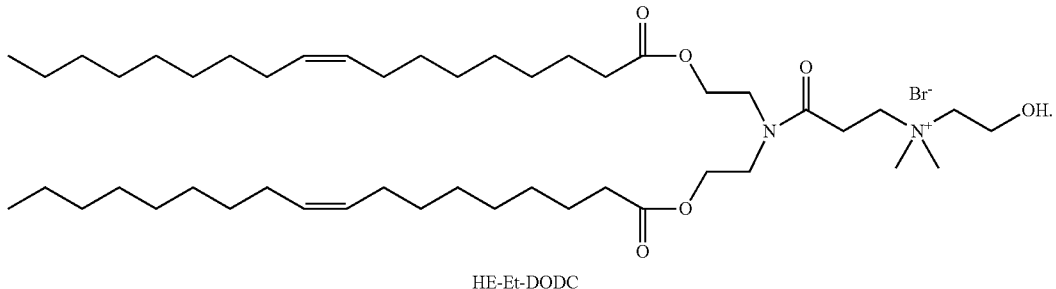

HE-Et-DODC

8. The method of claim 1, wherein the cationic lipid is selected from an ionizable cationic lipid or permanently charged cationic lipid.

9. The method of claim 1, wherein the lipid solution further comprises a compound selected from
a compound of the formula (A)

wherein
lipid (L) is selected from the group consisting of DSPE, DOPE, and DC;
linker (X) is selected from the group consisting of nothing, PEG550, PEG2000, PEG-glutamate (-Glu), Glu, C6, glycine, and GluNH, N1,N19-bis(3-(2-(2-(3-aminopropoxy)ethoxy)ethoxy)propyl)-4,7,10,13,16-pentaoxanonadecane-1,19-diamide; and
retinoid (R) is selected from the group consisting of tretinoin, adapalene, retinol, 4-hydroxy(phenyl)retinamide (4-HPR), retinoic acid, 9-(2,6,6-trimethylcyclohex-1-en-1-yl)nonanoic acid, 3,7-dimethyl-9-(2,6,6-trimethylcyclohex-1-en-1-yl)nonanoic acid, 3,7-dimethyl-9-(2,2,6-trimethylcyclohexyl)nonanoic acid, and any partially or fully saturated retinoid;
a compound of the formula (B)

wherein
linker (X) is N1,N19-bis(3-(2-(2-(3-aminopropoxy)ethoxy)ethoxy)propyl)-4,7,10,13,16-pentaoxanonadecane-1,19-diamide or N1,N19-bis(16,20-diamino-15-oxo-4,7,10-trioxa-14-azaicosyl)-4,7,10,13,16-pentaoxanonadecane-1,19-diamide; and
retinoid (R) is selected from the group consisting of tretinoin, adapalene, retinol, 4-hydroxy(phenyl)retinamide (4-HPR), and retinoic acid, 9-(2,6,6-trimethylcyclohex-1-en-1-yl)nonanoic acid, 3,7-dimethyl-9-(2,6,6-trimethylcyclohex-1-en-1-yl)nonanoic acid, 3,7-dimethyl-9-(2,2,6-trimethylcyclohexyl) nonanoic acid, and any partially or fully saturated retinoid.

10. The method of claim 1, wherein the population of lipid nanoparticles is prepared at 25-55° C.

11. The method of claim 1, wherein the aqueous solution comprises citrate, pH 3.5-6.5.

12. The method of claim 1, wherein the lipid solution is added to the aqueous solution by injection to an air-water interface.

13. The method of claim 1, wherein the lipid solution is added to the aqueous solution by a submerged injection.

14. A pharmaceutical formulation comprising the population of lipid nanoparticles produced by the method of claim 1.

15. The pharmaceutical formulation of claim 14, wherein the population of lipid nanoparticles has a nucleic acid:lipid ratio 0.06 to 0.16 (w:w), and a nucleic acid:lipid charge ratio of 1:2.5 to 1:1, and the cationic lipid is 40 to 60 mole percent of the lipids.

16. The pharmaceutical formulation of claim 14, wherein the cationic lipid is selected from the group consisting of

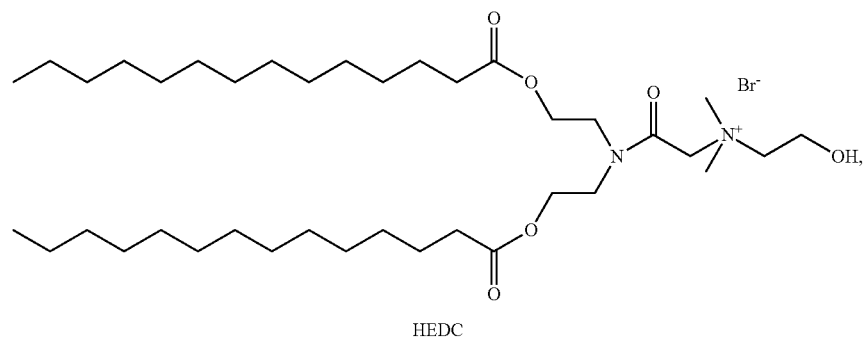

HEDC

-continued

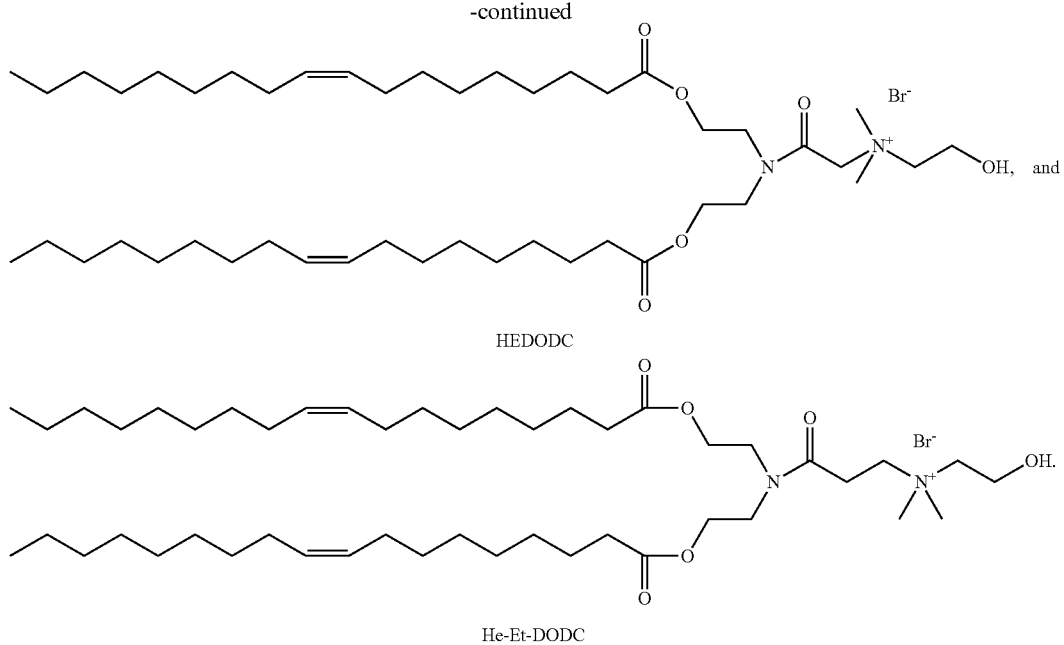

HEDODC

He-Et-DODC

17. The pharmaceutical formulation of claim 14, wherein the cationic lipid is selected from an ionizable cationic lipid or permanently charged cationic lipid.

18. The pharmaceutical formulation of claim 14, wherein the lipids further comprise a compound selected from a compound of the formula (A)

L—X—R  (A)

wherein
  lipid (L) is selected from the group consisting of DSPE, DOPE, and DC;
  linker (X) is selected from the group consisting of nothing, PEG550, PEG2000, PEG-glutamate (-Glu), Glu, C6, glycine, and GluNH, N1,N19-bis(3-(2-(2-(3-aminopropoxy)ethoxy)ethoxy)propyl)-4,7,10,13,16-pentaoxanonadecane-1,19-diamide; and
  retinoid (R) is selected from the group consisting of tretinoin, adapalene, retinol, 4-hydroxy(phenyl)retinamide (4-HPR), retinoic acid, 9-(2,6,6-trimethylcyclohex-1-en-1-yl)nonanoic acid, 3,7-dimethyl-9-(2,6,6-trimethylcyclohex-1-en-1-yl)nonanoic acid, 3,7-dimethyl-9-(2,2,6-trimethylcyclohexyl)nonanoic acid, and any partially or fully saturated retinoid;
a compound of the formula (B)

R—X—R  (B)

wherein
  linker (X) is N1,N19-bis(3-(2-(2-(3-aminopropoxy)ethoxy)ethoxy)propyl)-4,7,10,13,16-pentaoxanonadecane-1,19-diamide or N1,N19-bis(16,20-diamino-15-oxo-4,7,10-trioxa-14-azaicosyl)-4,7,10,13,16-pentaoxanonadecane-1,19-diamide; and
  retinoid (R) is selected from the group consisting of tretinoin, adapalene, retinol, 4-hydroxy(phenyl)retinamide (4-HPR), and retinoic acid, 9-(2,6,6-trimethylcyclohex-1-en-1-yl)nonanoic acid, 3,7-dimethyl-9-(2,6,6-trimethylcyclohex-1-en-1-yl)nonanoic acid, 3,7-dimethyl-9-(2,2,6-trimethylcyclohexyl) nonanoic acid, and any partially or fully saturated retinoid.

19. The pharmaceutical formulation of claim 14, wherein the process further comprises lyophilization of the population of lipid nanoparticles.

20. The pharmaceutical formulation of claim 14, further comprising a polysaccharide.

21. The pharmaceutical formulation of claim 20, wherein the polysaccharide consists of sucrose, trehalose, mannitol, sorbitol, xylitol, lactose, maltose, or inulin.

22. The pharmaceutical formulation of claim 14, wherein the mean particle diameter of the population of lipid nanoparticles is 50-100 nm.

23. The pharmaceutical formulation of claim 14, wherein the population of lipid nanoparticles has a polydispersity index less than 0.15.

* * * * *

UNITED STATES PATENT AND TRADEMARK OFFICE
CERTIFICATE OF CORRECTION

PATENT NO. : 10,155,945 B2
APPLICATION NO. : 15/430387
DATED : December 18, 2018
INVENTOR(S) : Victor Knopov et al.

Page 1 of 1

It is certified that error appears in the above-identified patent and that said Letters Patent is hereby corrected as shown below:

In the Claims

In Claim 2, Column 32, Line 23, after "claim" delete "of".

In Claim 4, Column 32, Line 28, after "claim" delete "of".

Signed and Sealed this
Eleventh Day of June, 2019

Andrei Iancu
*Director of the United States Patent and Trademark Office*